US009266807B1

(12) United States Patent
Norman et al.

(10) Patent No.: US 9,266,807 B1
(45) Date of Patent: Feb. 23, 2016

(54) CONVERSION OF ALCOHOLS TO LONGER CHAIN ALDEHYDES OR ALCOHOLS

(71) Applicant: Eastman Chemical Company, Kingsport, TN (US)

(72) Inventors: David William Norman, Cary, NC (US); Gerald Charles Tustin, Kingsport, TN (US); Jonathan Michael Penney, Gray, TN (US); Andrew James Vetter, Kingsport, TN (US); Venkata Bharat Ram Boppana, Johnson City, TN (US)

(73) Assignee: Eastman Chemical Company, Kingsport, TN (US)

(*) Notice: Subject to any disclaimer, the term of this patent is extended or adjusted under 35 U.S.C. 154(b) by 0 days.

(21) Appl. No.: 14/586,094

(22) Filed: Dec. 30, 2014

(51) Int. Cl.
*C07C 45/49* (2006.01)
*C07C 41/56* (2006.01)
*C07C 29/16* (2006.01)
*B01J 23/22* (2006.01)
*B01J 23/44* (2006.01)
*B01J 23/80* (2006.01)
*B01J 27/128* (2006.01)
*B01J 31/22* (2006.01)
*B01J 31/24* (2006.01)
*C07C 41/50* (2006.01)
*C07C 29/34* (2006.01)

(52) U.S. Cl.
CPC .............. *C07C 45/49* (2013.01); *B01J 23/22* (2013.01); *B01J 23/44* (2013.01); *B01J 23/80* (2013.01); *B01J 27/128* (2013.01); *B01J 31/2282* (2013.01); *B01J 31/24* (2013.01); *C07C 29/34* (2013.01); *C07C 41/50* (2013.01); *B01J 2531/845* (2013.01); *B01J 2540/40* (2013.01); *B01J 2540/50* (2013.01); *C07C 2531/02* (2013.01); *C07C 2531/18* (2013.01)

(58) Field of Classification Search
CPC ...... C07C 45/49; C07C 45/515; C07C 41/56; C07C 29/16
USPC ......... 568/45, 486, 487, 594, 672, 902.2, 905
See application file for complete search history.

(56) References Cited

U.S. PATENT DOCUMENTS

| 2,727,902 | A | | 12/1955 | Reppe et al. |
| 3,119,880 | A | * | 1/1964 | Kollar et al. ............... 568/905 |
| 4,239,705 | A | | 12/1980 | Pretzer et al. |
| 4,293,718 | A | | 10/1981 | Gauthier-Lafaye et al. |
| 4,306,091 | A | | 12/1981 | Gauthier-Lafaye et al. |
| 4,361,706 | A | | 11/1982 | Habib et al. |
| 4,374,285 | A | | 2/1983 | Lin et al. |
| 4,374,752 | A | * | 2/1983 | Argento et al. ............... 502/162 |
| 4,389,532 | A | | 6/1983 | Larkins, Jr. et al. |
| 4,400,551 | A | | 8/1983 | Keim et al. |
| 4,484,002 | A | | 11/1984 | Lin |
| 4,556,744 | A | | 12/1985 | Griggs et al. |
| 4,954,665 | A | | 9/1990 | Vidal |
| 5,364,979 | A | * | 11/1994 | Radlowski et al. ............ 568/697 |
| 5,770,541 | A | | 6/1998 | Vanderspurt et al. |
| 5,856,592 | A | * | 1/1999 | Hagen ....................... 568/902.2 |
| 5,908,807 | A | | 6/1999 | Vanderspurt et al. |
| 5,939,352 | A | | 8/1999 | Vanderspurt et al. |
| 6,034,141 | A | | 3/2000 | Vanderspurt et al. |
| 7,700,192 | B2 | | 4/2010 | Matthews et al. |
| 7,700,813 | B2 | | 4/2010 | Kourtakis et al. |
| 7,745,672 | B2 | | 6/2010 | Kourtakis et al. |
| 8,304,587 | B2 | | 11/2012 | Warner et al. |
| 2007/0293695 | A1 | | 12/2007 | Zoeller et al. |

FOREIGN PATENT DOCUMENTS

| CN | 101703926 A | 5/2010 |
| DE | 33 43 519 A1 | 6/1985 |
| DE | 35 06 714 A1 | 8/1986 |
| EP | 0 037 586 A1 | 10/1981 |
| FR | 697 726 | 1/1931 |

(Continued)

OTHER PUBLICATIONS

Bahrmann, Helmut; "Homologation—3.2 Special Catalysts and Processes"; Applied Homogeneous Catalysis Organometallic Compounds, vol. 2; pp. 902-914; 1996.

Cuigai, Liu, et al.; "Effect of Double Promoters on $CuO/SiO_2$ Catalyst for Synthesis of Isobutyraidehyde from Methanol and Ethanol"; Petrochemical Technology; pp. 550-553; 2011 (original language and English abstract).

Dinka, P. et al.; "Reaction of methanol and n-propanol over hydrotalcite-like catalysts containing vanadium oxide"; Applied Clay Science, vol. 13; pp. 467-477; 1998.

Gauthier-Lafaye, Jean and Perron, Robert; "Chapter 4 Synthesis of acetaldehyde and ethanol"; methanol and carbonylation; pp. 39-96; 1987.

Gauthier-Lafaye, J. et al.; "Methanol Hydrocarbonylation into Acetaldehyde Catalyzed by Cobalt and Two Different Iodides"; Journal of Molecular Catalysis, vol. 17; pp. 339-347; 1982.

(Continued)

*Primary Examiner* — Sikarl Witherspoon
(74) *Attorney, Agent, or Firm* — James Arnold, Jr.

(57) ABSTRACT

Processes are provided for contacting at least one $C_n$ alcohol equivalent having n carbon atoms and at least one $C_{n+1}$ alcohol equivalent having (n+1) carbon atoms with a Guerbet catalyst to form a product composition comprising a product compound having the structure:

IV

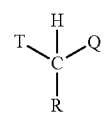

wherein:
C is a carbon atom;
H is a hydrogen atom;
Q is an alcohol or aldehyde group having one carbon;
R is a linear alkyl group having n carbon atoms; and
T is an alkyl group having (n−1) carbon atoms, except that when n=1, T is methyl.

47 Claims, No Drawings

(56) References Cited

FOREIGN PATENT DOCUMENTS

| FR | 697 727 | 1/1931 |
|---|---|---|
| FR | 697 896 | 1/1931 |
| JP | 2000 172854 | 6/2000 |

OTHER PUBLICATIONS

Girard, James W. et al.; "Technical Advantages of Vandium SCR Systems for Diesel NOx Control in Emerging Markets"; SAE Int. J. Fuels Lubr, vol. 1, Issue 1; pp. 488-494; 2008.

Guerbet; "Action of Ethyl, Isobutyl, Isoamyl Alcohols on their Sodium Derivatives"; Compt. Rend., vol. 128; pp. 1002-1004; 1899.

Hong, H. et al.; "Study of $V_2O_6$ Catalyst Deactivation for the Synthesis of Isobutyraldehyde from Methanol and Ethanol"; Chemical Engineering of Oil & Gas, vol. 37, No. 1; pp. 5-8; Feb. 2008 (original language and English abstract).

Hong, H. et al.; "Macrokinetics of Synthesis of Isobutyraldehyde from Methanol and Ethanol over $V_2O_5$ Catalyst"; Chemical Engineering of Oil & Gas, vol. 37, No. 5, pp. 370-372; Oct. 2008 (original language and English abstract).

Keim, W.; "Carbon monoxide: feedstock for chemicals, present and future"; Journal of Organometallic Chemistry, vol. 372; pp. 15-23; 1989.

Lehtinen, Christel et al.; "Experimental and computational studies on solvent effects in reactions of peracid-aldehyde adducts"; Tetrahedron, vol. 57; pp. 4741-4751; 2001.

Loevenich, Heinz and Röper, Michael; "Kinetic Studies of Methanol Homologation Using Cobalt-Phosphine-Iodine Catalysts"; $C_1$ Molecular Chemistry, vol. 1; pp. 155-170; 1984.

Matsu-Ura, Toyomi, et al.; "Guerbert Reaction of Primary Alcohols Leading to β-Alkylated Dimer Alcohols Catalyzed by Iridium Complexes"; Journal of Org. Chem., vol. 71, pp. 8306-8308; 2006.

Mizoroki, Tsutomu et al.; "Further Study of Methanol Carbonylation Catalyzed by Cobalt, Rhodium, and Iridium Catalysts": Bulletin of the Chemical Society of Japan, vol. 52, No. 2; pp. 479-482; 1979.

Moloy, Kenneth G. and Wegman, Richard W.; "Rhodium-Catalyzed Reductive Carbonylation of Methanol"; Organometallics, vol. 8; pp. 2883-2892; 1989.

Ogo, Shuhei, et al.; "Selective synthesis of 1-butanol from ethanol over strontium phosphate hydroxyapatite catalysts"; Appliced Catalysts A: General; vol. 402; pp. 188-195; 2011.

Reddy, B. Mahipal et al.; "A Single-Step Synthesis of Isobutyraldehyde from Methanol and Ethanol over CuO-ZnO-$Al_2O_3$ Catalyst"; Journal Chemical Society, Chemical Commun.; pp. 997-998; 1992.

Reddy, B. M. et al.; "Vapour Phase Synthesis of Isobutyraldehyde from Methanol and Ethanol over Mixed Oxide Supported Vanadium Oxide Catalysts"; Res. Chem. Intermed., vol. 23, No. 8; pp. 703-713; 1997.

Sharutin, V. V. et al.; "Synthesis and Structure of Cobalt Complexes $[Me_3EtN]+_2 [CoI_4]^{2-}$ and $[Me_3BuN]+_2[CoI_4]^{2-}$"; Russian Journal of Inorganic Chemistry, vol. 56, No. 9, pp. 1384-1389; 2011.

Twigg, Martyn V.; "Progress and future challenges in controlling automotive exhaust gas emissions"; Applied Catalysis B: Environmental, vol. 70; pp. 2-15; 2007.

Wang, Fey-Long and Lin, Yi-Hsuan; "Alkylation of Acetaldehyde with Methanol over Titanium Oxide-Supported Vanadium Oxide "; Chemistry Letters; p. 1867-1868; 1992.

Wang, Fey-Long, et al.; "Alkylation of aldehydes with methanol over titanium oxide catalysts"; Catalysis Letters, vol. 42; pp. 155-160; 1996.

Wang, Hui-Ying, et al.; "$V_2O_5/TiO_2$-$SiO_2$ Catalysts for the Synthesis of Isobutyraldehyde from Methanol and Ethanol"; Journal of Shenyang Institute of Chemical Technology, vol. 22, No. 3, pp. 200-203; Sep. 2008 (original language and English abstract).

Wender, Irving et al.; "Ethanol from Methanol"; Science, vol. 113; pp. 206-207; Feb. 23, 1951.

Wegman, Richard W. and Busby, David C.; "The Role of Phosphines and Solvents in $CoI_2$ - Catalyzed Reductive Carbonylation of Methanol"; Journal of Molecular Catalysis, vol. 32; pp. 125-136; 1985.

Co-pending U.S. Appl. No. 14/585,884, filed Dec. 30, 2014; Penny et al.

Notice of Allowance dated Jun. 10, 2015 received in U.S. Appl. 14/585,884.

Co-pending U.S. Appl. No. 14/586,070, filed Dec. 30, 2014; Vetter et al.

Non-Final Office Action dated June. 9, 2015 received in U.S. Appl. No. 14/586,070.

Co-pending U.S. Appl. No. 14/585,915, filed Dec. 30, 2014: Vetter et al.

Co-pending U.S. Appl. No. 14/585,940, filed Dec. 30, 2014: Penny et al.

Non-Final Office Action dated Jun. 9, 2015 received in U.S. Appl. No. 14/585,940.

\* cited by examiner

CONVERSION OF ALCOHOLS TO LONGER CHAIN ALDEHYDES OR ALCOHOLS

BACKGROUND OF THE INVENTION

Branched aldehydes and alcohols have a number of significant industrial uses. Isobutyraldehyde, for example, is useful as a precursor to isobutanol, isobutyric acid and coalescent molecules, all of which have a variety of uses. Isobutanol is used, for example, in a number of fuels, coatings, solvents and cleaners, as well as in making isobutyl acetate and p-xylene, and as an intermediate in making ester solvents and plasticizers. Higher molecular weight aldehydes and alcohols such as 2-methylbutyraldehyde, 2-methyl-1-butanol, 2-ethylpentanal, and 2-ethyl-1-pentanol are useful either as precursors in the flavors and fragrances industry, as components in personal care product formulations, or as precursors to low volatility plasticizers and paint coalescents.

Isobutyraldehyde is commonly made through the hydroformylation of propylene. As such, isobutyraldehyde, and therefore its derivative isobutanol, is subject to risks regarding changes in price or availability of propylene. Selective hydroformylation of butene and hexene to produce 2-methylbutyraldehyde and 2-ethylpentanal, respectively, remains a synthetic chemistry challenge. Identification of alternate routes to these compounds remains a priority, and identification of routes that would avoid dependency on olefin availability would be useful. Conversion of simple low cost alcohols such as methanol, ethanol and propanol to these value added aldehydes and alcohols are therefore of interest.

BRIEF SUMMARY OF THE INVENTION

The invention provides processes for preparing product compounds that include alcohols, aldehydes or combinations (blends) of alcohols and aldehydes using a Guerbet catalyst. In some embodiments, the invention provides processes that comprise contacting hydrogen, carbon monoxide, and a primary alkyl alcohol having n carbon atoms (in which n is selected from 1, 2 or 3) in the presence of a reductive carbonylation catalyst to form a crude reductive carbonylation product, and contacting at least one $C_{n+1}$ alcohol equivalent having (n+1) carbon atoms and at least one $C_n$ alcohol equivalent having n carbon atoms with a Guerbet catalyst to form a product composition comprising at least one product molecule. The crude reductive carbonylation product comprises at least one $C_{n+1}$ alcohol equivalent having (n+1) carbon atoms and at least one $C_n$ alcohol equivalent having n carbon atoms, and contacting the at least one $C_n$ alcohol equivalent and the at least one $C_{n+1}$ alcohol equivalent with the Guerbet catalyst comprises contacting the crude reductive carbonylation product or a portion thereof with the Guerbet catalyst. The reductive carbonylation catalyst comprises a complex of cobalt, iodide, and an onium cation or an alkali metal cation of the general formula $Y_2CoI_4$, wherein Y is the onium cation or the alkali metal cation. The total number of moles of the at least one $C_n$ alcohol equivalent contacted with the Guerbet catalyst is at least equal to the number of moles one $C_{n+1}$ alcohol equivalent contacted with the Guerbet catalyst and, if n=1, is equal to at least 2.0 multiplied by the number of moles of one $C_{n+1}$ alcohol equivalent contacted with the Guerbet catalyst. The at least one product molecule has the structure of formula IV:

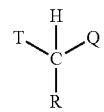

IV wherein:

C is a carbon atom;

H is a hydrogen atom;

Q is an alcohol or aldehyde group having one carbon;

R is a linear alkyl group having n carbon atoms; and

T is an alkyl group having (n−1) carbon atoms, except that when n=1,

T is methyl.

In some embodiments, the invention provides processes comprising contacting at least one $C_n$ alcohol equivalent having n carbon atoms and at least one $C_{n+1}$ alcohol equivalent having (n+1) carbon atoms (in which n=1, 2 or 3) with a Guerbet catalyst to form a product composition comprising at least one product molecule. The total number of moles of the at least one $C_n$ alcohol equivalent contacted with the Guerbet catalyst is at least equal to the number of moles one $C_{n+1}$ alcohol equivalent contacted with the Guerbet catalyst and, if n=1, is equal to at least 2.0 multiplied by the number of moles one $C_{n+1}$ alcohol equivalent contacted with the Guerbet catalyst. At least some of the at least one $C_n$ alcohol equivalent and at least some of the least one $C_{n+1}$ alcohol equivalent are within or derived from a crude reductive carbonylation product, the crude reductive carbonylation product being a product of contacting hydrogen, carbon monoxide, and a primary alkyl alcohol having n carbon atoms in the presence of a reductive carbonylation catalyst, the reductive carbonylation catalyst comprising a complex of cobalt, iodide, and an onium cation or an alkali metal cation of the general formula $Y_2CoI_4$, wherein Y is the onium cation or the alkali metal cation. The at least one product molecule has the structure of formula IV described above.

The invention further provides processes comprising contacting at least one dialkyl acetal compound with a Guerbet catalyst to form a product composition comprising at least one product molecule. The dialkyl acetal compound is the dialkyl of a linear alkyl aldehyde having (n+1) carbon atoms and comprises two linear alkoxy groups having n carbon atoms, in which n=1, 2 or 3. The at least one product compounds has the structure of formula IV above.

DETAILED DESCRIPTION

The invention provides processes in which at least one $C_n$ alcohol equivalent having n carbon atoms and at least one $C_{n+1}$ alcohol equivalent having (n+1) carbon atoms, in which n is 1, 2 or 3, are contacted with a Guerbet catalyst, to form a product composition comprising at least one product molecule. The total number of moles of the at least one $C_n$ alcohol equivalent contacted with the Guerbet catalyst is at least equal to the number of moles of one $C_{n+1}$ alcohol equivalent contacted with the Guerbet catalyst and, if n=1, is equal to at least 2.0 multiplied by the number of moles of one $C_{n+1}$ alcohol equivalent contacted with the Guerbet catalyst. The at least one product molecule has the structure of formula IV:

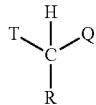

wherein:
C is a carbon atom;
H is a hydrogen atom;
Q is an alcohol or aldehyde group having one carbon;
R is a linear alkyl group having n carbon atoms; and
T is an alkyl group having (n−1) carbon atoms, except that when n=1,
T is methyl.

In some embodiments of the invention, at least some of the at least one $C_n$ alcohol equivalent and at least some of the least one $C_{n+1}$ alcohol equivalent are within a crude reductive carbonylation product or a portion thereof. The crude reductive carbonylation product is a product of contacting hydrogen, carbon monoxide, and a primary alkyl alcohol having n carbon atoms in the presence of a reductive carbonylation catalyst, the reductive carbonylation catalyst comprising a complex of cobalt, iodide, and an onium cation or an alkali metal cation of the general formula $Y_2CoI_4$, wherein Y is the onium cation or the alkali metal cation.

In some embodiments of the invention, the method includes the reductive carbonylation step as well as the step of contacting at least one $C_n$ alcohol equivalent and at least one $C_{n+1}$ alcohol equivalent with a Guerbet catalyst to form a product composition comprising at least one product molecule. In the reductive carbonylation step, hydrogen, carbon monoxide, and a primary alkyl alcohol having n carbon atoms are contacted in the presence of a reductive carbonylation catalyst to form a crude reductive carbonylation product comprising at least one $C_{n+1}$ alcohol equivalent having (n+1) carbon atoms and at least one $C_n$ alcohol equivalent having n carbon atoms. The reductive carbonylation catalyst comprises a complex of cobalt, iodide, and an onium cation or an alkali metal cation of the general formula $Y_2CoI_4$, wherein Y is the onium cation or the alkali metal cation. In such methods, "n" is selected from 1, 2 or 3 and the total number of moles of the at least one $C_n$ alcohol equivalent contacted with the Guerbet catalyst is at least equal to the number of moles of one $C_{n+1}$ alcohol equivalent contacted with the Guerbet catalyst and, if n=1, is equal to at least 2.0 multiplied by the number of moles of one $C_{n+1}$ alcohol equivalent contacted with the Guerbet catalyst. The at least one product molecule has the structure of formula (IV) described above.

Thus, in some embodiments, the invention provides processes comprising:
(a) contacting hydrogen, carbon monoxide, and a primary alkyl alcohol having n carbon atoms in the presence of a reductive carbonylation catalyst to form a crude reductive carbonylation product comprising at least one $C_{n+1}$ alcohol equivalent having (n+1) carbon atoms and at least one $C_n$ alcohol equivalent having n carbon atoms, wherein the reductive carbonylation catalyst comprises a complex of cobalt, iodide, and an onium cation or an alkali metal cation of the general formula $Y_2CoI_4$, wherein Y is the onium cation or the alkali metal cation;
(b) contacting at least one $C_{n+1}$ alcohol equivalent and at least one $C_n$ alcohol equivalent with a Guerbet catalyst to form a product composition comprising at least one product molecule, wherein:
n is selected from 1, 2 or 3;
the total number of moles of the at least one $C_n$ alcohol equivalent contacted with the Guerbet catalyst is at least equal to the number of moles one $C_{n+1}$ alcohol equivalent contacted with the Guerbet catalyst and, if n=1, is equal to at least 2.0 multiplied by the number of moles one $C_{n+1}$ alcohol equivalent contacted with the Guerbet catalyst;
contacting the at least one $C_n$ alcohol equivalent and the at least one $C_{n+1}$ alcohol equivalent with the Guerbet catalyst comprises contacting the crude reductive carbonylation product or a portion thereof with the Guerbet catalyst; and the at least one product molecule has the structure of formula IV above.

In some embodiments of the invention, n is 1 or 2. In some embodiments of the invention n is 1. When n is 1, the at least one product compound includes isobutyraldehyde, isobutanol, or both. When n is 2, the at least one product compound includes 2-methylbutyraldehyde, 2-methyl-1-butanol, or both. When n is 3, the at least one product compound includes 2-ethylpentanal (2-ethylvaleraldehyde), 2-ethyl-1-pentanol, or both.

When n=1, the at least one product compound includes isobutyraldehyde, isobutanol, or both compounds, in some embodiments instead of or in amounts much greater than propionaldehyde, n-propanol or both. For this reason, when n=1, T in Formula IV above is methyl rather than hydrogen. While not wanting to be bound by a particular theory, it is believed that this structure results from a second Guerbet reaction occurring between $C_1$ alcohol equivalents with propionaldehyde, n-propanol or both of the molecules.

In some embodiments, the invention provides a process comprising contacting at least one $C_n$ alcohol equivalent having n carbon atoms and at least one $C_{n+1}$ alcohol equivalent having (n+1) carbon atoms with a Guerbet catalyst to form a product composition comprising at least one product molecule, wherein:
the total number of moles of the at least one $C_n$ alcohol equivalent contacted with the Guerbet catalyst is at least equal to the number of moles one $C_{n+1}$ alcohol equivalent contacted with the Guerbet catalyst and, if n=1, is equal to at least 2.0 multiplied by the number of moles of one $C_{n+1}$ alcohol equivalent contacted with the Guerbet catalyst;
n=1, 2 or 3;
at least some of the at least one $C_n$ alcohol equivalent and at least some of the least one $C_{n+1}$ alcohol equivalent are within or derived from a crude reductive carbonylation product, the crude reductive carbonylation product being a product of contacting hydrogen, carbon monoxide, and a primary alkyl alcohol having n carbon atoms in the presence of a reductive carbonylation catalyst, the reductive carbonylation catalyst comprising a complex of cobalt, iodide, and an onium cation or an alkali metal cation of the general formula $Y_2CoI_4$, wherein Y is the onium cation or the alkali metal cation; and the at least one product molecule has the structure of formula IV above.

In some embodiments, the invention provides processes comprising contacting at least one dialkyl acetal compound with a Guerbet catalyst to form a product composition comprising at least one product molecule, wherein the dialkyl acetal compound is the dialkyl of a linear alkyl aldehyde having (n+1) carbon atoms and the dialkyl acetal comprises two linear alkoxy groups having n carbon atoms, n=1, 2 or 3 and wherein the at least one product molecule has the structure of formula IV above.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are intended to be reported precisely in view of methods of measurement. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the denomination of process steps, ingredients, or other aspects of the information disclosed or claimed in the application with letters, numbers, or the like is a convenient means for identifying discrete activities or ingredients and the recited lettering can be arranged in any sequence, unless otherwise indicated.

As used herein, the singular forms "a", "an", and "the" include plural referents unless the context clearly dictates otherwise. For example, reference to a $C_n$ alcohol equivalent is intended to include multiple types of $C_n$ alcohol equivalents. Thus, even use of language such as "at least one" or "at least some" in one location is not intended to imply that other uses of "a", "an", and "the" excludes plural referents unless the context clearly dictates otherwise. Similarly, use of the language such as "at least some" in one location is not intended to imply that the absence of such language in other places implies that "all" is intended, unless the context clearly dictates otherwise.

As used herein the term "and/or", when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "crude reductive carbonylation product", as used herein, refers to the products of reacting an alcohol having n carbon atoms with hydrogen and carbon monoxide in the presence of a sufficient concentration of hydrogen to result in reaction products that include an aldehyde having n+1 carbon atoms, an alkyl alcohol having n+1 carbon atoms, or a combination of the two and the sum of the mole percent of aldehydes having n+1 carbon atoms in the reaction product and the mole percent of alcohols having n+1 carbon atoms in the reaction product is greater than the mole percent of carboxylic acids having n+1 carbon atoms in the reaction product. The crude reductive carbonylation product comprises the many different compounds produced under reductive carbonylation conditions. The crude reductive carbonylation product is the liquid effluent directly exiting a carbonylation reactor, before any separation of the homogeneous catalyst or other liquid compounds. The crude reductive carbonylation product comprises the aldehyde having n+1 carbon atoms and/or the alkyl alcohol having n+1 carbon atoms as well as unreacted feed, other byproducts, and the catalyst.

The term "catalyst", as used herein, has its typical meaning to one skilled in the art as a substance that increases the rate of chemical reactions without being consumed.

The term "complex", "coordination complex" and "metal complex" as used herein, are equivalent terms which have their typical meaning to one skilled in the art as a metal ion and a surrounding array of bound molecules.

The term "onium cation", as used herein, refers to a cation selected from quaternary atoms or radicals such as quaternary ammonium, quaternary phosphonium, trialkyl sulfonium, and alkylated sulfoxide. The onium cation can also be of N-alkylated pyridinium. The term "onium salt", as used herein refers to a salt containing an onium cation. One skilled in the art will recognize that the disclosure of any onium salt necessarily and simultaneously discloses the corresponding onium cation.

The term "alkali metal cation", as used herein, refers to a group one element of the periodic table excluding hydrogen having at least one more proton than electron.

The term "phosphine ligand", as used herein, refers to an organic compound composed of hydrocarbyl groups covalently bound to one or more phosphorus atoms in the +3 oxidation state such that the lone pair of at least one of the phosphorus atoms binds the cobalt when dissolved in solution with cobalt. Such ligands are commonly referred to as tertiary phosphine since the phosphorus atom is substituted by three groups.

The term "bridged by" a number of atoms, as used herein, refers to the smallest number of consecutive atoms in a path between two atoms, specifically the two phosphorus atoms. For example, 1,3-bis(diphenyl phosphino)propane is bridged by 3 carbon atoms, 1,4-bis(diphenyl phosphino) butane is bridged by 4 carbon atoms, 1,2-bis(diphenylphosphino)benzene is bridged by 2 carbon atoms, bis(diphenylphosphinomethyl)biphenyl is bridged by 6 carbon atoms, and 1,1,1-tris (diphenylphosphinomethyl)ethane is bridged by 3 carbon atoms.

The term "alkylene", as used herein, refers to an alkylenediyl group having free valences at each group end to bond to the two phosphorus atoms. The terms "cycloalkylene", "arylene", and "biarylene" are used in a like manner. When the term "substituted or unsubstituted" is followed by a listing of hydrocarbon groups, the term is intended to modify each group. When a listing of hydrocarbon groups is followed by the term, "each having up to [a number of] carbon atoms", the term is intended to modify each group. The term "substituted", as used herein, has its usual meaning in the art, as in the hydrogen on the hydrocarbon may be substituted with the stated group. The term "heteroatom", as used herein has its usual meaning in the art, as an atom, such as nitrogen, oxygen, sulfur, or phosphorous, substituted for a carbon atom in a hydrocarbon.

The term "co-catalyst" as used herein, refers to a second catalyst which impacts the reaction rate and/or the selectivity to a given product.

The term "alkyl" as used herein refers to a group containing one or more saturated carbon atoms, such as methyl, ethyl, n-propyl, isopropyl, n-butyl, iso-butyl, tert-butyl and the like.

Thus, an "alkyl alcohol" refers to the structure R—OH wherein R is a group containing carbon atoms in which all bonds between carbon atoms are unsaturated. A "linear alkyl group" refers to an alkyl group having no branching of carbon atoms. Thus, n-butyl is a linear alkyl group while isobutyl is not. Thus, a "linear alkyl aldehyde" has the structure R—CHO, in which R is either H or an unbranched group in which carbon atoms are connected by single bonds. A "primary alkyl alcohol" refers to an alkyl alcohol in which the —OH group is attached to a terminal carbon. For example, n-propanol is a primary alkyl alcohol while isopropanol is not.

The term "Guerbet catalyst" refers to a catalyst or group of catalysts capable of catalyzing the series of reactions collectively known to persons skilled in the art as the Guerbet reaction. The Guerbet reaction is often described as a group of reactions that occur together in situ in which two primary alkyl alcohol molecules undergo sequential dehydrogenation, aldol condensation, and rehydrogenation to result in a primary branched aldehyde, or primary branched alcohol (and in which blends of the two can also be produced). However, the Guerbet reaction can also use the aldehydes of one or both of the two primary alkyl alcohols as a feed compound instead of or in addition to the alcohol itself. While not wanting to be bound to a particular theory, it has been suggested that this is because an early or initial step in the Guerbet reaction is the dehydrogenation of the reactant alcohols to their aldehydes, which would mean that feeding the linear alkyl aldehydes would allow the Guerbet reaction to proceed without that early or initial step. In some embodiments, the choice of Guerbet catalyst, or use of reactor pressure and temperature, hydrogen concentration, and reaction time can affect the product distribution of the Guerbet reaction. For example, some Guerbet catalysts have been described as producing mostly or entirely aldehyde while others have been described as producing mostly or entirely alcohol. In some embodiments, longer reaction times or higher reactor pressure, or both may lead to higher alcohol product concentration relative to the concentration of the aldehyde. Thus, the Guerbet reaction may be described according to the following simplified formula (excluding catalysts and other reactants, products and byproducts such as hydrogen and water):

$$A+B \rightarrow C$$

where:

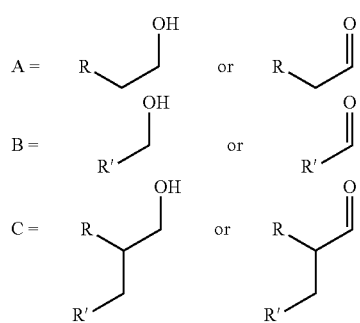

It will be understood that the Guerbet reaction may also proceed in embodiments where both the alcohol and aldehyde species of A, B or both A and B are present. It will further be understood as a general matter that the product of a Guerbet reaction may also include the product of two "A" molecules reacting with one another, the product of two "B" molecules reacting with each other, or both. It will likewise be understood that independent of whether A, B or both are in alcohol form, aldehyde form or both, the Guerbet reaction may result in either or both of the alcohol and aldehyde species of C.

As used throughout this application, "$C_n$ alcohol equivalents" shall mean $C_n$ primary alcohols (where n is the number of carbon atoms) and all compounds or groups of compounds that may provide or serve the same function as a $C_n$ alcohol as a feed to the Guerbet reaction. Similarly, "$C_{n+1}$ alcohol equivalents" shall mean the $C_{n+1}$ primary alcohols (where n is the number of carbon atoms) and all compounds or groups of compounds that may provide or serve the same function as the $C_{n+1}$ primary alcohol as a feed to the Guerbet reaction. For example, as explained above, the aldehyde of a $C_n$ primary alcohol may be contacted with a Guerbet catalyst and provide the same product or group of products that the $C_n$ primary alcohol would have provided under identical conditions. As such, the aldehyde of the $C_n$ primary alcohol is an equivalent for $C_n$ alcohol. Thus, for example, formaldehyde is a $C_1$ alcohol equivalent (equivalent to methanol), acetaldehyde is a $C_2$ alcohol equivalent (equivalent to ethanol) and propionaldehyde is a $C_3$ alcohol equivalent (equivalent to n-propanol).

$C_n$ alcohol equivalents may also be found in molecules that will react to produce $C_n$ primary alcohols or aldehydes thereof under the reactant conditions of the Guerbet process. The same is true for $C_{n+1}$ alcohol equivalents. Thus, $C_n$ alcohol equivalents or $C_{n+1}$ alcohol equivalents may be parts of a larger molecule such that a single molecule may contain both types of equivalents, a plurality of a single type of equivalent, or both. It has been found, for example, that a dialkyl acetal compound that: (a) is the dialkyl acetal of a linear alkyl aldehyde having (n+1) carbon atoms; and (b) comprises two linear alkoxy groups having n carbon atoms, reacts in a Guerbet reaction, to provide a compound having the structure of formula IV above. Thus, in reactions in which n=1, the dimethyl acetal of acetaldehyde reacts in a Guerbet reaction to provide isobutyraldehyde and isobutanol via reaction of two methanol (i.e. $C_n$ alcohol) equivalents with one ethanol (i.e. $C_{n+1}$ alcohol) equivalent. Without wishing to be bound to a theory, it is believed that, the two methoxy groups may leave the acetal as methanol groups, leaving the acetaldehyde (an ethanol equivalent). As another example, it is known that paraldehyde is a cyclic trimer of acetaldehyde that will react to provide three acetaldehydes (ethanol equivalents) under Guerbet reaction conditions.

In some embodiments the crude reductive carbonylation product (or portion thereof) that is contacted with the Guerbet catalyst comprises a dialkyl acetal of an aldehyde, the aldehyde being a linear alkyl aldehyde having (n+1) carbon atoms, and the dialkyl acetal comprising two linear alkoxy groups having n carbon atoms. In some embodiments, the dialkyl acetal of the linear alkyl aldehyde comprises at least about 30 molar percent of the total of all $C_{n+1}$ alcohol equivalents present in the crude reductive carbonylation product (or portion thereof) that is contacted with the Guerbet catalyst. In some embodiments, the dialkyl acetal of the linear alkyl aldehyde comprises at least about 20, at least about 25, at least about 40, at least about 50, at least about 60, at least about 70, at least about 80 or at least about 90 molar percent of all $C_{n+1}$ alcohol equivalents present in the crude reductive carbonylation product (or portion thereof) that is contacted with the Guerbet catalyst. In some embodiments, the dialkyl acetal of the linear alkyl aldehyde comprises from 20 to 99, from 20 to 95, from 30 to 99, from 50 to 99, from 20 to 50, from 50 to 60, from 60 to 70, from 70 to 80, from 80 to 90, from 90 to 99, from 80 to 99, from 70 to 99 or from 60 to 99 molar percent of all $C_{n+1}$ alcohol equivalents present in the crude reductive carbonylation product (or portion thereof) that is contacted with the Guerbet catalyst.

In some embodiments, alkoxy groups on the dialkyl acetal of the linear alkyl aldehyde comprise at least about 5 molar percent to of the total of all $C_n$ alcohol equivalents present in the crude reductive carbonylation product (or portion thereof) that is contacted with the Guerbet catalyst. In some embodiments, alkoxy groups on the dialkyl acetal of the linear alkyl aldehyde comprise at least about 10, at least about 15, at least about 20, at least about 25, at least about 30, at least about 40, at least about 50, at least about 60, at least about 70, at least about 80, or at least about 90 molar percent of the $C_n$ alcohol equivalent present in the crude reductive carbonylation product (or portion thereof) that is contacted with the Guerbet catalyst. In some embodiments, alkoxy groups on the dialkyl acetal of the linear alkyl aldehyde comprise from 5 to 25 molar percent of all $C_n$ alcohol equivalents present in the crude reductive carbonylation product (or portion thereof) that is contacted with the Guerbet catalyst. In some embodiments, alkoxy groups on the dialkyl acetal of the linear alkyl aldehyde comprise from 5 to 10, from 5 to 15, from 5 to 20, from 5 to 25, from 10 to 20, from 10 to 25, from 10 to 30, from 10 to 40, from 10 to 50, from 10 to 60, from 20 to 50, from 20 to 30, from 30 to 40, from 40 to 50, from 50 to 60, from 60 to 70, from 70 to 80, from 80 to 90, from 80 to 95, from 90 to 99 or from 10 to 99 molar percent of all $C_n$ alcohol equivalents present in the crude reductive carbonylation product (or portion thereof) that is contacted with the Guerbet catalyst.

As explained above, when n=1, the at least one product molecule includes isobutyraldehyde, isobutanol, or both compounds because of a second Guerbet reaction of the $C_1$ alcohol equivalents with propionaldehyde, n-propanol or both of the molecules. As a result, for embodiments in which n=1, propionaldehyde and n-propanol can each be formed by the reaction of a $C_n$ alcohol equivalent and a $C_{n+1}$ alcohol equivalent, needing only another reaction with another $C_n$ equivalent to produce isobutyraldehyde, isobutanol or both. As such, when n=1, propionaldehyde and n-propanol would each properly be considered as containing both a $C_n$ alcohol equivalent and a $C_{n+1}$ alcohol equivalent. Tables 1, 2 and 3 provide a listing of $C_n$ alcohol equivalents and $C_{n+1}$ alcohol equivalents where n=1, n=2, and n=3, respectively.

TABLE 1

EQUIVALENTS (n = 1)

| Abbreviation | Full Name | Number of Methanol ($C_n$ alcohol Equivalents | Number of Ethanol ($C_{n+1}$ alcohol Equivalents |
|---|---|---|---|
| HAc | Acetaldehyde | 0 | 1 |
| HCO2Me | Methyl formate | 1 | 0 |
| HPr | n-Propionaldehyde | 1 | 1 |
| (MeO)2Et/ DMA | 1,1-dimethoxy ethane/ Dimethylacetal | 2 | 1 |
| MeOAc | Methyl acetate | 1 | 0 |
| 1,1-(EtO)-(MeO)Et | 1,1-Methoxyethoxy ethane | 1 | 2 |
| (EtO)2Et | 1,1-Diethoxy ethane | 0 | 3 |
| EtOAc | Ethyl acetate | 0 | 1 |
| MeOH | Methanol | 1 | 0 |
| EtOH | Ethanol | 0 | 1 |
| (MeO)2Bu | 1,1-Dimethoxy butane | 2 | 0 |

TABLE 1-continued

EQUIVALENTS (n = 1)

| Abbreviation | Full Name | Number of Methanol ($C_n$ alcohol Equivalents | Number of Ethanol ($C_{n+1}$ alcohol Equivalents |
|---|---|---|---|
| 1,1-(EtO)-(MeO)Bu | 1,1-Methoxyethoxy butane | 1 | 1 |
| nPrOH | n-Propanol | 1 | 1 |
| Paraldehyde | Paraldehyde | 0 | 3 |
| (EtO)2Bu | 1,1-Diethoxy butane | 0 | 2 |

TABLE 2

EQUIVALENTS (n = 2)

| Abbreviation | Full Name | Number of Ethanol ($C_n$ alcohol Equivalents | Number of Propanol ($C_{n+1}$ alcohol Equivalents |
|---|---|---|---|
| HPr | n-Propionaldehyde | 0 | 1 |
| (EtO)2Pr | 1,1-Diethoxy propane | 2 | 1 |
| EtOPr | Ethyl propionate | 1 | 0 |
| 1,1-(EtO)-(PrO)Pr | 1,1-Ethoxypropoxy propane | 1 | 2 |
| (PrO)2Pr | 1,1-Dipropoxy propane | 0 | 3 |
| PrOPr | Propyl propionate | 0 | 1 |
| EtOH | Ethanol | 1 | 0 |
| PrOH | n-Propanol | 0 | 1 |
| (EtO)2Hex | 1,1-Diethoxy hexane | 2 | 0 |
| 1,1-(EtO)-(PrO)Hex | 1,1-Ethoxypropoxy hexane | 1 | 1 |
| (PrO)2Hex | 1,1-Dipropoxy hexane | 0 | 2 |
| Et3Trioxane | 2,4,6-triethyl-1,3,5-trioxane | 0 | 3 |

TABLE 3

EQUIVALENTS (n = 3)

| Abbreviation | Full Name | Number of Propanol ($C_n$ alcohol Equivalents | Number of Butanol ($C_{n+1}$ alcohol Equivalents |
|---|---|---|---|
| HBu | n-Butyraldehyde | 0 | 1 |
| (PrO)2Bu | 1,1-Dipropoxy butane | 2 | 1 |
| PrOBu | Propyl butyrate | 1 | 0 |
| 1,1-(PrO)-(BuO)Pr | 1,1-Propoxybutoxy propane | 1 | 2 |
| (BuO)2Bu | 1,1-Dibutoxy butane | 0 | 3 |
| BuOBu | Butyl butyrate | 0 | 1 |
| PrOH | n-Propanol | 1 | 0 |
| BuOH | n-Butanol | 0 | 1 |
| (PrO)2Oct | 1,1-Dipropoxy octane | 2 | 0 |
| 1,1-(PrO)-(BuO)Oct | 1,1-Butoxypropoxy octane | 1 | 1 |

TABLE 3-continued

| | | EQUIVALENTS (n = 3) | |
|---|---|---|---|
| Abbreviation | Full Name | Number of Propanol ($C_n$ alcohol Equivalents) | Number of Butanol ($C_{n+1}$ alcohol Equivalents) |
| (BuO)2Oct | 1,1-Dibutoxy octane | 0 | 2 |
| Pr3Trioxane | 2,4,6-tripropyl-1,3,5-trioxane | 0 | 3 |

Reductive Carbonylation Reaction

In the reductive carbonylation reaction, hydrogen and carbon monoxide, are contacted with a primary alkyl alcohol having 1, 2 or 3 carbon atoms in the presence of a reductive carbonylation catalyst to form a crude reductive carbonylation product containing at least one $C_{n+1}$ alcohol equivalent having (n+1) carbon atoms and at least one $C_n$ alcohol equivalent having n carbon atoms. The reductive carbonylation catalyst comprises a complex of cobalt, iodide, and an onium cation or an alkali metal cation of the general formula $Y_2CoI_4$, wherein Y is the onium cation or the alkali metal cation.

The primary alkyl alcohol is selected from methanol, ethanol and n-propanol. In some embodiments of the invention, the primary alkyl alcohol is methanol. In some embodiments of the invention, the primary alkyl alcohol is ethanol. In some embodiments of the invention, the primary alkyl alcohol is n-propanol.

The reductive carbonylation catalyst comprises a complex of cobalt, iodide, and an onium cation or an alkali metal cation of the general formula $Y_2CoI_4$, where Y is an onium cation or an alkali metal cation. The reductive carbonylation catalyst complex can be readily synthesized by those skilled in the art. For example, an onium iodide salt or alkali metal iodide salt can be reacted with cobalt(II) iodide as illustrated in the reaction below.

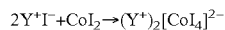

$$2Y^+I^- + CoI_2 \rightarrow (Y^+)_2[CoI_4]^{2-}$$

When an onium salt is used to produce the complex, the onium salt can comprise an onium cation selected from quaternary atoms or radicals such as quaternary ammonium, quaternary phosphonium, trialkyl sulfonium, and alkylated sulfoxide. The onium salt compound can be functional and includes protonated forms of the atoms or radicals, especially protonated forms of various tertiary amines and tertiary phosphines. The onium salt can contain any number of carbon atoms, e.g., up to about 60 carbon atoms, and also can contain one or more heteroatoms. The tri- and tetra-alkyl quaternary ammonium and phosphonium salts typically contain a total of about 5 to 40 carbon atoms. One skilled in the art understands that the listing of the onium salts simultaneously gives a listing of the onium cations (e.g., if onium salt methyltriphenylphosphonium iodide is disclosed, then onium cation methyltriphenylphosphonium is also disclosed).

Examples of an alkali metal cation include cations of lithium, sodium, potassium, rubidium and cesium. In some embodiments, the alkali metal cation can be lithium, sodium, potassium, rubidium, or cesium. In some embodiments, the alkali metal cation can be lithium, sodium, or potassium.

Examples of quaternary ammonium and phosphonium salts include salts having onium cations of the general formula (I)

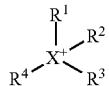

(I)

wherein X can be phosphorus (P) or nitrogen (N) and wherein $R^1$, $R^2$, $R^3$, and $R^4$ are independently selected from substituted or unsubstituted alkyl having up to 20 carbon atoms, substituted or unsubstituted cycloalkyl having 5 to 20 carbon atoms, or substituted or unsubstituted aryl having 6 to 20 carbon atoms.

In some embodiments, X is selected from phosphorus (P) and nitrogen (N), $R^1$ is methyl, and $R^2$, $R^3$, and $R^4$ are independently selected from alkyl having up to 12 carbon atoms and aryl. When $R^2$, $R^3$, and/or $R^4$ are aryl, the aryl is selected from only one of the group consisting of phenyl, tolyl, xylyl, and mesityl.

The quaternary ammonium salts can also be selected from salts of aromatic, heterocyclic onium cations having the general formula (II) or (III)

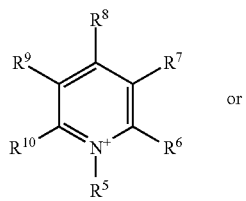

(II)

or

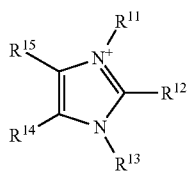

(III)

wherein at least one ring atom is a quaternary nitrogen atom and $R^6$, $R^7$, $R^8$, $R^9$, $R^{10}$, $R^{12}$, $R^{14}$, and $R^{15}$ are independently selected from hydrogen, substituted or unsubstituted alkyl having up to 20 carbon atoms, substituted or unsubstituted cycloalkyl having 5 to 20 carbon atoms, and substituted or unsubstituted aryl having 6 to 20 carbon atoms; and $R^5$, $R^{11}$, and $R^{13}$ are independently selected from substituted or unsubstituted alkyl having up to 20 carbon atoms, substituted or unsubstituted cycloalkyl having 5 to 20 carbon atoms, and substituted or unsubstituted aryl having about 6 to about 20 carbon atoms. In some embodiments, $R^5$ is methyl and $R^6$, $R^7$, $R^8$, $R^9$, and $R^{10}$ are hydrogen.

Examples of specific ammonium salts include tetrapentylammonium iodide, tetrahexylammonium iodide, tetraoctylammonium iodide, tetradecylammonium iodide, tetradodecylammonium iodide, tetrapropylammonium iodide, tetrabutylammonium iodide, methyltrioctylammonium iodide, methyltributylammonium iodide, N-octyl-quinuclidinium iodide, N,N'-dimethyl-N,N'-dihexadecylpiperazinium diiodide, dimethyl-hexadecyl-[3-pyrrolidinylpropyl]ammonium iodide, N,N,N,N',N',N'-hexa(dodecyl)octane-1,8-diammonium diiodide, N,N,N,N',N',N'-hexa(do-decyl)butane-1,4-diammonium diiodide; imidazolium iodides such as 1-butyl-3-methylimidazolium iodide, 1,3-dimethylimidazolium iodide, 1,3,4-trimethyl-imidazolium iodide, 1,2,3,4,5-pentamethylimidazolium iodide; pyridinium iodides such as N-octylpyridinium iodide, N-methylpyridinium iodide, N-methyl-2-picolinium iodide, N-methyl-3-picolinium iodide, N-methyl-4-picolinium iodide, N-methyl-5-ethyl-2-methyl-pyridinium iodide, N-methyl-3,4-lutidinium iodide; N-methyl quinolinium iodide, N-methyl isoquinolinium iodide or mixtures thereof. Preferred quaternary ammonium iodides include 1-butyl-3-methylimidizolium iodide, N-methyl pyridinium iodide, N-methyl-2-methyl pyridinium iodide, N-methyl-3-methyl pyridinium iodide, N-methyl-4-methyl pyridinium iodide, and 1,3-dimethylimidazolium iodide.

Exemplary phosphonium salts include tetraoctylphosphonium iodide, tetrabutylphosphonium iodide, triphenyl(hexyl)phosphonium iodide, triphenyl(octyl)phosphonium iodide, tribenzyl(octyl)phosphonium iodide, tribenzyl(dodecyl)phosphonium iodide, triphenyl(decyl)phosphonium iodide, triphenyl(dodecyl)phosphonium iodide, tetrakis(2-methylpropyl)phosphonium iodide, tris(2-methylpropyl)(butyl)phosphonium iodide, triphenyl(3,3-dimethylbutyl)phosphonium iodide, triphenyl(3-methylbutyl)phosphonium iodide, tris(2-methylbutyl)(3-methylbutyl)phosphonium iodide, triphenyl[2-trimethylsilylethyl]phosphonium iodide, tris(p-chlorophenyl)-(dodecyl)phosphonium iodide, hexyltris(2,4,6-trimethylphenyl)phosphonium iodide, tetradecyltris(2,4,6-trimethylphenyl)phosphonium iodide, dodecyltris(2,4,6-trimethylphenyl)phosphonium iodide, methyltrioctylphosphonium iodide, methyltributylphosphonium iodide, methyltricyclohexylphosphonium iodide, and the like. Preferred phosphonium iodides include methyltriphenylphosphonium iodide, methyltributylphosphonium iodide, and methyltrioctylphosphonium iodide.

In some embodiments, the onium cation can be of the general formula (I) or (II)

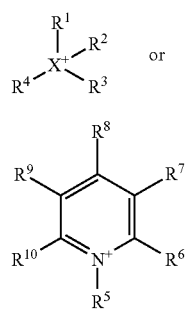

For formula (I), X is phosphorus (P) and $R^1$ is methyl. $R^2$, $R^3$, and $R^4$ are independently selected from alkyl having up to 12 carbon atoms and aryl selected from phenyl, tolyl, xylyl, or mesityl. When two or more of $R^2$, $R^3$, and/or $R^4$ are aryl, each aryl is the same. For formula (II), $R^5$ is methyl and $R^6$, $R^7$, $R^8$, $R^9$, and $R^{10}$ are hydrogen.

In some embodiments, the onium cation can be methyltriphenylphosphonium, methyltributylphosphonium, methyltrioctylphosphonium, or 1-methylpyridinium. In some embodiments, the onium cation can be methyltriphenylphosphonium, methyltributylphosphonium, or 1-methylpyridinium. In some embodiments, the onium cation can be methyltriphenylphosphonium or 1-methylpyridinium. In some embodiments, the complex can be bis(methyltriphenylphosphonium) cobalt tetraiodide, bis(methyltributylphosphonium) cobalt tetraiodide, or bis(1-methylpyridinium) cobalt tetraiodide.

In some embodiments of the invention, the onium salt can be generated from polymers containing a quaternary or quaternizable phosphine or amine. The onium salt polymer may be derived in whole or part from (or containing polymerized residues of) 2- or 4-vinyl-N-alkylpyridinium iodide or 4-(trialkylammonium)styrene iodide. For example, a variety of 4-vinyl pyridine polymers and copolymers are available, and may be quaternized or protonated with alkyl iodide or hydrogen iodide to generate heterogeneous onium salts. Further, polymers of N-methyl-4-vinylpyridinium chloride are commercially available and may be used as-is or are preferably exchanged with iodide to form the iodide salt. Several means for such exchange are known. The heterogeneous onium compound may comprise (1) an onium salt compound deposited on a catalyst support material or (2) of a polymeric material containing quaternary nitrogen groups. Examples of such polymeric onium compounds include polymers and copolymers of vinyl monomers which contain quaternary nitrogen (ammonium) groups. Polymers and copolymers derived from 2- and 4-vinyl-N-alkylpyridinium iodide, e.g., poly(4-vinyl-N-methylpyridinium iodide), are specific examples of such polymeric onium salt compounds. In this aspect, the onium cation would be a heterogeneous component in the reaction mixture.

In some embodiments, the reductive carbonylation catalyst comprises a cobalt complex of the type described above and a phosphine ligand. The phosphine ligand is a multidentate compound containing at least two bridged phosphorus atoms. The phosphine ligand can be of the general formula

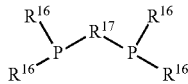

The phosphorus atoms P are bridged by 2 to 6 atoms of $R^{17}$. $R^{17}$ can be a substituted or unsubstituted alkylene, cycloalkylene, arylene and/or biarylene, each having up to 22 carbon atoms. $R^{17}$ can optionally contain one or more heteroatoms. The heteroatom can be nitrogen, oxygen, sulfur, phosphorus, or mixtures thereof. $R^{16}$ is a substituted or unsubstituted alkyl, alkoxy, cycloalkyl, aryl, and/or aryloxy, each having up to 20 carbon atoms.

The phosphorus atoms P "are bridged by" 2 to 6 atoms of $R^{16}$ which means that each of the two phosphorus atoms shown above are bonded to separate carbon atoms of $R^{17}$ such that the shortest molecular path between the two phosphorus atoms contains 2 to 6 atoms of $R^{16}$. These 2 to 6 atoms are referred to as bridging atoms. The bridging atoms can be carbon and/or heteroatom selected from nitrogen, oxygen, sulfur, phosphorus or mixtures thereof.

In one example, $R^{17}$ can be a straight- or branch-chain hydrocarbon radical containing 2 to 6 bridging atoms, where the bridging atoms can be substituted, for example, with alkyl, alkoxy, aryl, dialkylphosphinomethyl, diarylphosphino, or diarylphosphinomethyl.

In some embodiments, $R^{17}$ can be arylene or biarylene. The arylene or biarylene can be substituted, for example, with methyl, ethyl, propyl, iso-propyl, butyl, iso-butyl, methoxy, ethoxy, propoxy, iso-propoxy, butoxy, iso-butoxy, phenoxy, nitro, chloro, fluoro, trifluoromethyl. In some embodiments, the arylene or biarylene can be substituted with methyl, ethyl, propyl, or iso-propyl.

In some embodiments, $R^{16}$ can be a substituted alkyl, alkoxy, cycloalkyl, aryl, or aryloxy wherein the substituted group can be, for example, methyl, ethyl, propyl, iso-propyl, butyl, iso-butyl, methoxy, ethoxy, propoxy, iso-propoxy, butoxy, iso-butoxy, phenoxy, nitro, chloro, fluoro, or trifluoromethyl. In some embodiments, the substituted group can be methyl, ethyl, propyl, or iso-propyl.

In some embodiments, $R^{16}$ is chosen from phenyl, naphthyl, anthryl, tetrahydronaphthyl, or octahydronaphthyl each of which can be substituted with alkyl, alkoxy, aryl, aryloxy, halogen, or nitro. In some embodiments, $R^{16}$ can be methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, or mesityl-oxy Without representing an exhaustive list, specific examples of multidentate phosphine ligands useful in the present invention include 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,5-bis(diphenylphosphino)pentane; 1,2-bis(dicyclohexylphosphino)ethane; 1,3-bis(dicyclohexylphosphino)propane; 1,4-bis(dicyclohexylphosphino)butane; 1,5-bis(dicyclohexylphosphino)pentane; 1,6-bis(dicyclohexylphosphino)hexane; 1,2-bis(dimethylphosphino)ethane; 1,3-bis(dimethylphosphino)propane; 1,4-bis(dimethylphosphino)butane; 1,5-bis(dimethylphosphino)pentane; 1,6-bis(dimethylphosphino)hexane; 1,2-bis(diisopropylphosphino)ethane; 1,3-bis(diisopropylphosphino)propane; 1,4-bis(diisopropylphosphino)butane; 1,2-bis(di-tert-butylphosphine)ethane; 1,3-bis(di-tert-butylphosphine)propane; 1,4-bis(di-tert-butyl phosphine)butane; 2,2'-bis(diphenylphosphino)-1,1'-binaphthalene; 2,2'-bis(diphenylphosphino)-1,1'-biphenyl; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and/or 1,3-bis(diphenylphosphino)cyclobutane.

In some embodiments the phosphine ligand can be chosen from 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphine)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and/or 1,3-bis(diphenylphosphino)cyclobutane.

In some embodiments the phosphine ligand can be 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; and/or 1,1,1-tris(diethylphosphinomethyl)ethane. In some embodiments, the phosphine ligand can be 1,3-bis(diphenylphosphino)propane, 1,1,1,-tris(diphenylphosphinomethyl)ethane; and/or 1,1,1-tris(diethylphosphinomethyl)ethane.

In some embodiments, two phosphorus atoms of the phosphine ligand are bridged by saturated or unsaturated alkylene containing three carbon atoms. The phosphine ligand can be of the general formula

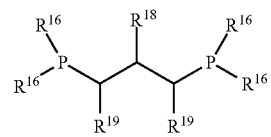

In some embodiments, $R^{18}$ can be a hydrogen radical or a hydrocarbon radical having up to 17 carbon atoms. The hydrocarbon radical can be substituted with alkyl, alkoxy, cycloalkyl aryl, aryloxy dialkylphosphinomethyl, diarylphosphinomethyl, or mixtures thereof. In some embodiments, $R^{18}$ can be a hydrogen radical, methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, mesityl-oxy, dimethylphosphinomethyl, diethylphosphinomethyl, di-n-propylphosphinomethyl, di-iso-propylphosphinomethyl, di-n-butylphosphinomethyl, di-iso-butyl phosphinomethyl, di-tert-butylphosphinomethyl, dimethoxyphosphinomethyl, diethoxyphosphinomethyl, d i-n-propoxyphosphinomethyl, di-iso-propoxyphosphinomethyl, d i-n-butoxyphosphinomethyl, di-iso-butoxyphosphinomethyl, di-tert-butoxyphosphinomethyl diphenylphosphinomethyl, ditolylphosphinomethyl, or dixylylphosphinomethyl.

$R^{19}$ can be a hydrogen radical or a substituted or unsubstituted alkyl, alkoxy, cycloalkyl, aryl, and aryloxy, each having up to 8 carbon atoms. In some embodiments, $R^{19}$ can be a hydrogen radical or a substituted or unsubstituted alkyl. In some embodiments, $R^{19}$ can be a hydrogen radical.

In some embodiments $R^{16}$ can be methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, or mesityl-oxy.

In some embodiments, $R^{16}$ or $R^{18}$ can be unsubstituted aryl, alkyl, cycloalkyl, alkoxy, or aryloxy substituted, for example, with groups selected from methyl, ethyl, propyl, iso-propyl, butyl, iso-butyl, methoxy, ethoxy, propoxy, iso-propoxy, butoxy, iso-butoxy, phenoxy, nitro, chloro, fluoro, and/or trifluoromethyl.

In some embodiments, $R^{16}$ or $R^{18}$ can be aryl groups chosen from phenyl, naphthyl, anthryl, tetrahydronaphthyl, and/or octahydronaphthyl with any of the groups substituted with alkyl, alkoxy, aryl, aryloxy, halogen, and/or nitro.

In some embodiments, the phosphorus atoms are bridged by saturated or unsaturated alkylene containing three carbon atoms. The phosphine ligand can be of the general formula

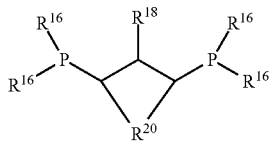

$R^{20}$ can be a substituted or unsubstituted alkyl having up to 8 carbon atoms, forming a cycloalkyl group between the phosphorus atoms. $R^{18}$ is a hydrogen radical and $R^{16}$ is selected from the group consisting of methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, and mesityl-oxy.

The invention includes all combinations of the components described above. Thus, any of the onium compounds described above may be used with any of the ligands described above. In some embodiments, the onium cation can be methyltriphenylphosphonium, methyltributylphosphonium, methyltrioctylphosphonium, and/or 1-methylpyridinium and the phosphine ligand can be 1,3-bis(diphenylphosphino)propane, 1,1,1-tris(diphenylphosphinomethyl)ethane, and/or 1,1,1-tris(diethylphosphinomethyl)ethane. In some embodiments, the onium cation is methyltriphenylphosphonium and the phosphine ligand is 1,3-bis(diphenylphosphino)propane.

In some embodiments, the molar ratio of the phosphine ligand to the cobalt (phosphine ligand:cobalt) ranges from 0.025:1 to 2:1. In other examples, the molar ratio of phosphine ligand to cobalt (phosphine ligand:cobalt) ranges from 0.025:1 to 0.5:1 or 0.025:1 to 1:1 or 0.025:1 to 1.5:1 or 0.1:1 to 1:1 or 0.1:1 to 0.1:1.5, or 1:1 to 2:1.

In some embodiments, a hydrogenation co-catalyst is used with any of the embodiments of the reductive carbonylation catalyst described above. This co-catalyst can be chosen from any metal capable of hydrogenating an aldehyde such as iridium, rhodium, or ruthenium, with ruthenium being most often used. The source of ruthenium is not particularly limiting and can be chosen from many commercially available materials such as ruthenium(III) acetylacetonate, ruthenium trichloride, triruthenium dodecacarbonyl, 1,1,1-tris(diphenylphosphinomethyl)ethane ruthenium dicarbonyl, and/or ruthenium(IV)oxide hydrate. In some embodiments the co-catalyst can be triruthenium dodecacarbonyl, 1,1,1-tris(diphenyl phosphinomethyl)ethane ruthenium dicarbonyl, or ruthenium(IV)oxide hydrate. In some embodiments, the co-catalyst is present in an amount ranging from 0.0001 moles to 10 moles of co-catalyst per 100 moles of alcohol. Other examples of co-catalyst concentration include 0.001 moles to 5 moles of co-catalyst per 100 moles of alcohol and 0.001 moles to 2 moles of co-catalyst per 100 moles of alcohol.

In some embodiments of the invention, the reductive carbonylation catalyst includes a phosphonium iodide. The term "phosphonium iodide", as used herein, refers to quaternary phosphonium cation with an iodide anion. The phosphonium iodide is not particularly limited and can be the same or different from the phosphonium iodide used to produce the cobalt complex. The phosphonium iodide can be selected from methyltriphenylphosphonium iodide, methyltributylphosphonium iodide, methyltrioctylphosphonium iodide, butyltridodecylphosphonium iodide, tetraoctylphosphonium iodide, tetrabutylphosphonium iodide, triphenyl(hexyl)phosphonium iodide, triphenyl(octyl)phosphonium iodide, tribenzyl(octyl)phosphonium iodide, tribenzyl(dodecyl) phosphonium iodide, triphenyl(decyl)phosphonium iodide, triphenyl(dodecyl)-phosphonium iodide, tetrakis(2-methylpropyl)phosphonium iodide, tris(2-methylpropyl)-(butyl) phosphonium iodide, triphenyl(3,3-dimethylbutyl)-phosphonium iodide, triphenyl(3-methylbutyl)phosphonium iodide, tris(2-methylbutyl)-(3-methyl-butyl)-phosphonium iodide, triphenyl[2-trimethylsilylethyl]phosphonium iodide, tris(p-chlorophenyl)-(dodecyl) phosphonium iodide, hexyltris(2,4,6-trimethyl-phenyl)phosphonium iodide, tetradecyltris(2,4,6-trimethyl-phenyl)phosphonium iodide, dodecyltris(2,4,6-trimethylphenyl)phosphonium iodide, methyltrioctylphosphonium iodide, methyltributylphosphonium iodide, and methyltricyclohexylphosphonium iodide. In some embodiments, the phosphonium iodide can be selected from methyltriphenylphosphonium iodide, methyltributylphosphonium iodide, methyltrioctylphosphonium iodide, and butyltridodecylphosphonium iodide. In some embodiments, the phosphonium iodide can be selected from methyltriphenylphosphonium iodide, methyltributylphosphonium iodide, and methyltrioctylphosphonium iodide. In some embodiments, the phosphonium iodide comprises methyltriphenylphosphonium.

Depending on the type of catalyst composition used, the amount of catalyst composition can be measured in terms of the moles of cobalt, the moles of phosphine ligand (where present), the moles of phosphonium iodide (where present), the molar ratio of phosphine ligand to cobalt (phosphine ligand:cobalt), and/or the molar ratio of phosphonium iodide to cobalt (phosphonium iodide:cobalt). In some embodiments, the cobalt is present in an amount ranging from 0.001 moles to 50 moles of cobalt per 100 moles of methanol. Other examples of cobalt concentration include 0.001 moles to 10 moles of cobalt per 100 moles of methanol, 0.01 moles to 5 moles of cobalt per 100 moles of methanol, 0.01 moles to 2 moles of cobalt per 100 moles of methanol, and 0.02 moles to 5 moles of cobalt per 100 moles of methanol. In some embodiments, the molar ratio of the phosphine ligand to the cobalt (phosphine ligand:cobalt) ranges from 0.025:1 to 2:1. In other examples, the molar ratio of phosphine ligand to cobalt (phosphine ligand:cobalt) ranges from 0.025:1 to 0.5:1 or 0.025:1 to 1:1 or 0.025:1 to 1.5:1 or 0.1:1 to 1:1 or 0.1:1 to 0.1:1.5, or 1:1 to 2:1. In some embodiments, the molar ratio of the phosphonium iodide to the cobalt (phosphonium iodide:cobalt) ranges from 0.1:1 to 50:1. In other examples, the molar ratio of phosphonium iodide to cobalt (phosphonium iodide:cobalt) ranges from 0.1:1 to 20:1 or 0.1:1 to 10:1 or 0.1:1 to 5:1 or 1:1 to 50:1 or 1:1 to 20:1 or 1:1 to 10:1 or 1:1 to 1.5:1.

The reductive carbonylation can be conducted under continuous, semi-continuous, and batch modes of operation and can utilize a variety of reactor types. The term "continuous" as used herein means a process wherein reactants are introduced and products withdrawn simultaneously in an uninterrupted manner. By "continuous" it is meant that the process is substantially or completely continuous in operation and is to be contrasted with a "batch" process. "Continuous" is not meant in any way to prohibit normal interruptions in the continuity of the process due to, for example, start-up, reactor maintenance, or scheduled shut down periods. The term "batch" process as used herein means a process wherein all the reactants are added to the reactor and then processed according to a predetermined course of reaction during which no material is fed to or removed from the reactor. The term "semicontinuous" means a process where some of the reactants are charged at the beginning of the process and the remaining reactants are fed continuously as the reaction progresses. Alternatively, a semicontinuous process may also include a process similar to a batch process in which all the reactants are added at the beginning of the process except that one or more of the products are removed continuously as the reaction progresses.

Any effective carbonylation reactor designs or configurations may be used in carrying out the process provided by the present invention. Examples of suitable reactor types include, but are not limited to, stirred tank, continuous stirred tank, tower, and tubular reactors. The process also may be practiced in a batchwise manner by contacting the low molecular weight alcohol, hydrogen and carbon monoxide with the present catalyst composition in an autoclave.

The reductive carbonylation process can be carried out over a range of temperatures. For example, the reductive carbonylation process can be carried out at a temperature ranging from 100° C. to 250° C. In other examples, the process can be carried out at a temperature ranging from 150° C. to 230° C., or ranging from 170° C. to 210° C.

The reductive carbonylation process can be carried out over a range of pressures. For example, the process can be carried out at a pressure ranging from 100 kPa (15 psig) to 60 MPa (8700 psig). In other examples, the reductive carbonylation process can be carried out at a pressure ranging from 1 MPa (150 psig) to 40 MPa (5800 psig) or ranging from 6.9 MPa (1000 psig) to 34 MPa (4900 psig).

In some embodiments of the invention, the contacting of the hydrogen, carbon monoxide, and alcohol can occur in the presence of a solvent. The solvent is not particularly limiting so long as it is acceptably inert under reaction conditions. In some embodiments, the solvent is present and selected from alkanes and arenes having 6 to 20 carbon atoms, ketones having 5 to 20 carbon atoms, esters having 5 to 20 carbon atoms, ethers having 5 to 20 carbon atoms, and alkyl carbonate esters having from 3 to 20 carbon atoms. Some representative examples of the solvent include, but are not limited to, hexane, heptane, octane, decane, benzene, toluene, xylenes, methyl napththalenes, 3-methyl-2-butanone, methyl isobutyl ketone (also known as 4-methyl-2-pentanone), methyl isopropyl ketone, methyl propyl ketone, diisobutyl ketone, isobutylisobutyrate, ethyl acetate, n-butyl acetate, isobutylacetate, isopropylacetate, n-propyl acetate, diisopropylether, dibutylether, tertiary-amyl methyl ether, tertiary-butyl methyl ether, and mixtures thereof. In some embodiments of our invention, the solvent can be toluene, heptane, cyclohexane, ethylbenzene, diethyl ether, or 4-methylanisol.

The molar ratio of carbon monoxide to hydrogen ($CO:H_2$) in the reductive carbonylation process can vary over a wide range. For example, $CO:H_2$, can range from 1:1 to 1:10. In other examples, $CO:H_2$ ranges from 1:1 to 1:5 or 1:1 to 1:2.

Crude Reductive Carbonylation Product

The reductive carbonylation process produces a crude reductive carbonylation product as defined above. In some embodiments, the amount of methyl iodide in the crude reductive carbonylation product is significantly less than in typical methanol reductive carbonylation processes. In some embodiments, the crude reductive carbonylation product comprises less than 1 weight percent methyl iodide, based on the total weight of the crude reductive carbonylation product. In other embodiments, the crude reductive carbonylation product comprises less than 0.8 weight percent, less than 0.5 weight percent, less than 0.1 weight percent, less than 0.05 weight percent, less than 100 parts per million (ppm), less than 50 ppm, less than 10 ppm, less than 100 parts per billion (ppb), less than 50 ppb, or less than 10 ppb of methyl iodide, based on the total weight of the crude reductive carbonylation product. These very low levels are advantageous for the claimed process because iodine compounds can be catalyst "poisons" that deactivate or shorten the life of some Guerbet catalysts.

The crude reductive carbonylation product contains at least one $C_n$ alcohol equivalent and at least one $C_{n+1}$ alcohol equivalent. In some embodiments, the total number of moles of the at least one $C_n$ alcohol equivalent in the crude reductive carbonylation product is at least equal to the number of moles one $C_{n+1}$ alcohol equivalent in the crude reductive carbonylation product and, if n=1, is equal to at least 2.0 multiplied by the number of moles one $C_{n+1}$ alcohol equivalent in the crude reductive carbonylation product. The use of "total number of moles the at least one" in reference to a type of compound means the sum of the number of moles for all molecules within that type of molecule. For example, if n=1 and 10 moles of ethanol and 20 moles of acetaldehyde are present, the total number of moles the at least one $C_{n+1}$ alcohol equivalent is 30. In some embodiments, the total number of moles of the at least one $C_n$ alcohol equivalent in the crude reductive carbonylation product is less than the number of moles one $C_{n+1}$ alcohol equivalent in the crude reductive carbonylation product and, if n=1, is less than 2.0 multiplied by the number of moles one $C_{n+1}$ alcohol equivalent in the crude reductive carbonylation product.

As explained in the definition above, the crude reductive carbonylation product or portion thereof may also contain unreacted portions of the $C_n$ primary alkyl alcohol and other products of the reductive carbonylation process. For example, the $C_{n+1}$ alcohol as well as one or more of the $C_n$ alcohol equivalents and $C_{n+1}$ alcohol equivalents for the reaction may be present in various amounts and combinations. Water is a byproduct of the reductive carbonylation reaction and thus will also be present unless removed by a further processing (e.g. a separation process or a subsequent reaction). In some embodiments in which the di-$C_n$-alkyl acetal of the $C_{n+1}$ aldehyde is present, the presence of water during the Guerbet reaction may be useful in converting the di-$C_n$-alkyl acetal of the $C_{n+1}$ to one or more product compound. For example, equilibration of the acetal molecule back into its constituent components is dependent on the presence of water in the crude reductive carbonylation product.

Some other examples of components of the crude reductive carbonylation product may include $C_n$ alkyl carboxylic acid (e.g., acetic acid when n=1), di-$C_n$-alkyl ether (e.g., dimethyl ether when n=1), $C_n$-alkyl, $C_{n+1}$-alkyl-ether (e.g., methylethyl ether when n=1), di-$C_{n+1}$-alkyl ether (e.g., diethyl ether when n=1), and longer chain products from $C_{n+1}$ aldehyde aldol condensation reactions (e.g., n-butyraldehyde, n-butanol, crotonaldehyde and crotyl alcohol when n=1). Further, in embodiments described above in which the contacting of the hydrogen, carbon monoxide, and alcohol can occur in the presence of a solvent, the solvent may be present in the crude reductive carbonylation product or portion thereof. In such embodiments, the crude reductive carbonylation product may contain a solvent selected from the above solvents and ranges. In embodiments in which a portion of the crude reductive carbonylation product is contacted with the Guerbet catalyst, such solvent may or may not be present in such portion. For example, the solvent may have been separated from the portion of the crude reductive carbonylation product that is contacted with the Guerbet catalyst, for example as a result of separation processes such as distillation, phase separation, extraction, decantation and membrane separation. In some embodiments, the portion of the crude reductive carbonylation product that is contacted with the Guerbet catalyst includes a solvent comprising a hydrocarbon compound that lacks functional groups that would react with the Guerbet catalyst. In some embodiments, selected from $C_6$ to $C_{10}$ alkanes and cycloalkanes, $C_6$ to $C_8$ ethers, $C_6$ to $C_{10}$ aryl and aralkyl compounds and combinations of two or more of the foregoing. Where used, the amount of solvent present can be present in an amount ranging from 5 vol % to 90 vol % based on the total volume of solvent and $C_n$ alcohol. In other examples, the solvent can be present in an amount ranging from 10 vol % to 80 vol %, 20 vol % to 60 vol %, or 30 vol % to 50 vol %, each based on the total volume of solvent and $C_n$ alcohol. The examples of possible components of the crude reductive carbonylation product described above are not intended to be a limiting or exhaustive list.

The crude reductive carbonylation product, or a portion thereof, is used in the subsequent step of contacting with the Guerbet catalyst. A "portion" of a crude reductive carbonylation product is a part of a crude reductive carbonylation product composition that is separated from other parts of the crude reductive carbonylation product (for example, from the reductive carbonylation catalyst) by any means, including means that result in the portion having a composition that is the same as that of the crude reductive carbonylation product prior to separation as well as means that result in the portion having a composition that is different from the crude reductive carbonylation product. Examples include portions obtained simply by piping or decanting part of the crude reductive carbonylation product as well as portions obtained by separation processes such as evaporation, distillation, extraction, membrane separation, or combinations of two or more of the following. In some embodiments, the portion of the crude reductive carbonylation product is obtained by one or more process steps that include separating it from the reductive carbonylation catalyst by evaporating the crude reductive carbonylation product. In some embodiments, the one or more process steps include distillation.

The crude reductive carbonylation product or portion thereof may be further processed in any desirable way prior to combining it with the Guerbet catalyst. Any effective or useful process or combination of processes for concentrating or separating constituents of the crude reductive carbonylation product can be used. Again, some examples include distillation, phase separation, extraction, decantation and membrane separation. It may be also combined with another composition if desired to adjust the molar ratio between $C_n$ alcohol equivalents per mole of $C_{n+1}$ alcohol equivalents. In some embodiments, the crude reductive carbonylation product does not have a total number of moles of the at least one $C_n$ alcohol equivalent in the crude reductive carbonylation product is at least equal to the number of moles one $C_{n+1}$ alcohol equivalent in the crude reductive carbonylation product and, if n=1, is equal to at least 2.0 multiplied by the number of moles one $C_{n+1}$ alcohol equivalent in the crude reductive carbonylation product, and supplemental $C_n$ alcohol equivalents are added to bring it to that ratio or higher above the ratio. As another example, a portion of the crude reductive carbonylation product prepared by evaporation may be condensed to liquid is desired for combination with the Guerbet catalyst. As yet another example a separation process may be used to remove undesired components or to concentrate desired components. Alternatively, it can be heated to an appropriate temperature for contacting it with the Guerbet reaction.

Contacting with a Guerbet catalyst $C_n$ alcohol equivalents and $C_{n+1}$ alcohol equivalents are contacted with the Guerbet catalyst. This is accomplished by contacting one or more feed streams or other compositions with the Guerbet catalyst. The consolidated content of all compositions combined with the Guerbet catalyst contain a total number of moles of the at least one $C_n$ alcohol equivalent that is at least equal to the number of moles one $C_{n+1}$ alcohol equivalent contacted with the Guerbet catalyst and, if n=1, is equal to at least 2.0 multiplied by the number of moles one $C_{n+1}$ alcohol equivalent contacted with the Guerbet catalyst. In some embodiments, the compositions combined with the Guerbet catalyst include only one or more crude reductive carbonylation product or portions thereof. In some embodiments, the compositions combined with the Guerbet catalyst include other components, compositions or streams in addition to the crude reductive carbonylation product or portion thereof. For example, if the crude reductive carbonylation product does not contain sufficient $C_n$ alcohol equivalents to provide the desired ratio of $C_n$ alcohol equivalents to $C_{n+1}$ alcohol equivalents, supplemental $C_n$ alcohol equivalents may be provided to provide a desired number of moles of $C_n$ alcohol equivalents. "Supplemental $C_n$ alcohol equivalents" simply mean $C_n$ alcohol equivalents that were not present in the crude reductive carbonylation product but are also contacted with the Guerbet catalyst, such as another composition containing $C_n$ alcohol equivalents. Any acceptable means of combining with the $C_{n+1}$ alcohol equivalents and $C_n$ alcohol equivalents with the Guerbet catalyst can be used. For example, in some embodiments in which a homogeneous Guerbet catalyst is used, a composition containing fresh, recycled or makeup catalyst may be fed to the reactor. In some embodiments, the homogeneous Guerbet catalyst can be dissolved in the crude reductive carbonylation product or portion thereof and delivered to the reactor with the reductive carbonylation product or portion thereof.

The Guerbet catalyst can be any effective catalyst that will cause the desired composition and product to form, including catalysts used in both homogeneous and heterogeneous processes. As used throughout this application, a "homogeneous process" refers to a process in which the catalyst and reactants are together in a single phase of matter, most commonly a liquid phase, and a "heterogeneous process" refers to processes in which the catalyst and reactants are in different phases of matter, as is the case with vapor phase reactants over a solid catalyst. In some embodiments, the $C_n$ alcohol equivalents and $C_{n+1}$ alcohol equivalents are reacted as a gas over a Guerbet catalyst that is in a solid phase. In some embodiments the $C_n$ alcohol equivalents and $C_{n+1}$ alcohol equivalents are reacted as a liquid over a Guerbet catalyst that is in a solid phase. The $C_n$ alcohol equivalents and $C_{n+1}$ alcohol equivalents can also be present in both liquid and gaseous phases. In some embodiments, the $C_n$ alcohol equivalents and $C_{n+1}$ alcohol equivalents are combined with the Guerbet catalyst in a liquid phase in which the Guerbet catalyst is dissolved, dispersed, suspended or otherwise contained.

Where a heterogeneous process is used, the catalyst can be any effective heterogeneous catalyst. Some examples of useful heterogeneous Guerbet catalysts include acid, base and acid-base bifunctional catalysts with the capacity to perform aldol condensation and transfer of hydrogen from alcohols to carbonyl groups. Some examples of solid catalysts useful for heterogeneous aldol processes include oxides, zeolites, hydrotalcites, hydroxyapatites, and anionic clays. Some examples of oxides include titanium oxide (titania), silicon oxide (silica), zirconia, sulfate modified zirconia, lanthanum oxide, copper oxide, zinc oxide, niobium oxide, cerium oxide, aluminum oxide (alumina), zirconium oxides, alkaline earth metal oxides (for example, magnesium oxide, barium oxide, strontium oxide or calcium oxide), alkali promoted alkaline earth metal oxides (such as lithium, sodium, potassium or cesium promoted magnesium oxide) and combinations thereof. Some examples of zeolites that can be used include clinoptilolite and zeolite X. Some examples of hydrotalcites include magnesium-aluminum hydrotalcites, and magnesium-aluminum hydrotalcites modified with Zn, Ni, Pd, Pt, Co, Fe, Cu, Cr or Ru ions. Some examples of hydroxyapatites include calcium phosphate hydroxyapatite, strontium phosphate hydroxyapatite, calcium vanadate hydroxyapatite, strontium vanadate hydroxyapatite and combinations thereof. Some examples of anionic clays include sjogrenite, pyroaurite, barbertonite and Meixnerite. In some embodiments, the catalyst contains titanium and oxygen.

The ability of the above-mentioned catalysts to perform Guerbet chemistry can be enhanced by addition of metals to the catalyst that facilitate transfer hydrogenation reactions. Some examples include addition of hydrogenation metals such as vanadium, copper, palladium, rhodium, ruthenium, nickel and platinum. Addition of oxides of vanadium, copper, palladium, rhodium, ruthenium, nickel and platinum to the catalyst may also improve Guerbet chemistry performance.

In some embodiments, the Guerbet catalyst is selected from amphoteric metal oxides modified with transition metals, wherein the amphoteric metal oxide is a catalyst for aldol condensation and the transition metal is a catalyst for the transfer of hydrogen from alcohols to carbonyl groups. For example, in some embodiments, the Guerbet catalyst is a titania catalyst of the general formula: $MTiO_2$ where M is the transition metal. The transition metal can be any metal known to have hydrogenation capacity such as V, Cr, Fe, Ru, Os, Co, Rh, Ir, Ni, Pd, Pt, Cu or Zn. The metal can be present either in elemental or oxidized form. For example, in some embodiments, the invention uses vanadium or palladium modified titania catalysts. Vanadium titania catalysts are typically written as $V_2O_5/TiO_2$ since the vanadium is pentavalent and present in oxide form. The catalysts can also be written as $V/TiO_2$ or V/Ti where it is understood that the V and Ti are present in oxidized forms. Such catalysts can be prepared by any means, and means for preparing them are known in the art.

The Guerbet heterogeneous isobutyraldehyde synthesis catalysts may also be composed of more than one metal (or metal oxide) deposited on a support. For example, alumina supported copper oxide-zinc oxide ($CuO—ZnO—Al_2O_3$) materials are known to be particularly useful for this invention and several methods of preparation are known. Copper oxide-zinc oxide catalysts supported on silica, titania, or zirconia are also effective for this reaction.

Any type of suitable reactor or reaction zone may be used. The reactor zone can be oriented vertically or horizontally. For vertically oriented reactor zones, the vapor feed may enter at the bottom and move up the reactor or may enter at the top and move down the reactor. Some examples of suitable reactors include fixed bed reactors, fluidized bed reactors, tubular reactors, stirred tank reactors, continuous stirred tank reactors, tower reactors, trickle bed reactors, Berty reactors and the like. The process also may be practiced in a batchwise manner by contacting the $C_n$ alcohol equivalents and $C_{n+1}$ alcohol equivalents are contacted with the heterogeneous Guerbet catalyst in an autoclave.

The reaction is performed under conditions effective to cause the $C_n$ alcohol equivalents and $C_{n+1}$ alcohol equivalents to react to form the product composition containing the product compound. In some embodiments of the invention, the temperature in the reaction zone in a heterogeneous Guerbet process can range from about 100° C. to about 500° C., or from about 200° C. to about 400° C., or from about 300° C. to about 375° C. The pressure in the reaction zone can be from about 0.1 to about 100 bar, from about 1 to about 50 bar or from about 5 bar to about 10 bar.

In some heterogeneous Guerbet reactions the feed or feeds can be delivered to the reaction zone in conjunction with a diluent gas. The diluent gas can comprise steam, methane, carbon dioxide, carbon monoxide, nitrogen, argon, oxygen, air, hydrogen, helium and mixtures thereof. The molar ratio of the diluent gas to the total moles of reactant feeds can range, for example from about 0.01:1 to about 20:1, from about 0.01:1 to about 10:1, from about 0.01:1 to about 5:1, from about 0.1:1 to about 20:1, from about 0.1:1 to about 10:1, or from about 0.1:1 to about 1:1. The flow rate of the reaction feed to the Guerbet reactor can be at a rate of about 1 to 50, 1 to 25 or 5-10 mmole/minute/mL of catalyst. The diluent gas can be fed to the Guerbet reactor at a rate of from 0.05 to 25, from 0.5 to 10 or from 1 to 5 mmole/minute/mL of catalyst.

In some embodiments, in the event of coke formation and catalyst inhibition the heterogeneous catalyst can be regenerated by treatment with air or oxygen at temperatures between 350° C. and 500° C. for 0.5 to 20 hours. Alternatively, the catalyst can be regenerated by treatment with hydrogen between 200° C. and 500° C. for 0.5 to 20 hours. The catalyst can be reused following the regeneration procedure.

Where a homogeneous Guerbet process is used, any effective homogeneous Guerbet catalyst can be used. Some examples include a transition metal based catalyst promoted by an alkali metal alkoxide co-catalyst. Some examples of such transition metal based catalysts include $[IrCl(cod)]_2$, $[Cp^*IrCl_2]_2$, $[Ir(OH)(cod)]_2$, $IrCl(PPh_3)_3$, $IrCl_3(3H_2O)$, $RhCl_3/PBu_3$, $[RuCl(eta6-p-cymene)]Cl$, $PdCl_2$ and $RuCl_2$. Some examples of alkali metal alkoxide co-catalysts useful with such catalysts include potassium hydroxide, potassium tert-butoxide and sodium butoxide.

Optionally, a Guerbet catalyst further includes one or more additional components such as ligands and promoters. In some embodiments that use a homogeneous Guerbet catalyst, for example, the Guerbet catalyst further comprises a ligand selected from phosphine compounds. Some examples include the phosphine ligands used in the reductive carbonylation catalyst of the claimed invention, but also include other phosphine compounds, such as 1,1-bis-diphenylphosphino methane. Thus, in some embodiments, the Guerbet catalyst comprises a ligand selected from 1,3-bis-diphenylphosphino propane, 1,2-bis-diphenylphosphino ethane and 1,1-bis-diphenylphosohino methane. In some embodiments that use a homogeneous Guerbet catalyst, for example, the Guerbet catalyst further comprises a promoter or co-catalyst, either with or without the ligands described above. Some examples of promoters that can be used include alkali metal alkoxides. In some embodiments, the alkali metal alkoxides are selected from lithium, sodium, or potassium salts of linear or branched alcohols having 1 to 18 carbon atoms. In some embodiments, the homogeneous Guerbet catalyst comprises a promoter selected from potassium tert-butoxide or sodium butoxide or sodium ethoxide.

In some embodiments, the activity and selectivity of the homogeneous Guerbet catalyst is aided by the addition of alkene and diene hydrogen acceptors to the Guerbet reaction. Some examples of suitable hydrogen acceptors include linear and branched aliphatic and aromatic hydrocarbons having 2 to 40 carbon atoms and contain one or more alkene groups that are readily hydrogenated by the Guerbet catalyst the corresponding alkane group during the Guerbet reaction. Some examples of these hydrogen acceptors are tert-butyl ethylene, 1-hexene, styrene, and 1,7-octadiene In some embodiments, contacting at least one $C_{n+1}$ alcohol equivalent and at least one $C_n$ alcohol equivalent with a homogeneous Guerbet catalyst occurs in the presence of a solvent. Any solvent that will not unacceptably interfere with the Guerbet reaction may be used. In some embodiments, the solvents are selected from saturated and unsaturated hydrocarbons, glycol diethers such as monoglyme, ethyl glyme, diglyme, proglyme, ethyl diglyme, or triglyme that do not contain functional groups that will react under homogeneous Guerbet reaction conditions. Some examples of reactive functional groups under Guerbet conditions include aldehydes, alcohols, or ketones since these would undergo base catalyzed aldol condensation reactions. The presence of such solvents is not required. In some embodiments, a liquid reactant such as the Cn+1 alcohol already present in the composition serves as a solvent.

In some embodiments, the temperature of homogeneous Guerbet reactions can be from about 25° C. to about 300° C., or from about 100° C. to about 250° C., or from about 150° C. to about 200° C. In some embodiments, the pressure in the homogeneous Guerbet reactor can be from about 0.1 to about 100 bar, from about 1 to about 50 bar or from about 5 bar to about 10 bar.

The step of contacting with the heterogeneous or homogeneous Guerbet catalyst can be conducted under continuous, semi-continuous, and batch modes of operation and can utilize a variety of reactor types. By "continuous" it is meant that the process is substantially or completely continuous in operation and is to be contrasted with a "batch" process. "Continuous" is not meant in any way to prohibit normal interruptions in the continuity of the process due to, for example, start-up, reactor maintenance, or scheduled shut down periods. The term "batch" process as used herein means a process wherein all the reactants are added to the reactor and then processed according to a predetermined course of reaction during which no material is fed to or removed from the reactor. The term "semicontinuous" means a process where some of the reactants are charged at the beginning of the process and the remaining reactants are fed continuously as the reaction progresses. Alternatively, a semicontinuous process may also include a process similar to a batch process in which all the reactants are added at the beginning of the process except that one or more of the products are removed continuously as the reaction progresses. In embodiments in which the process includes both reductive carbonylation and contacting with the Guerbet catalyst, these two steps may be different or the same in terms of being performed continuously, batchwise, or semicontinuously.

Additional materials may also be contacted with the Guerbet catalyst. Such materials may be combined into the crude reductive carbonylation product or portion thereof as discussed above, or may be fed separately to the reaction zone where the Guerbet catalyst is located. For example, in some embodiments the crude reductive carbonylation product or portion thereof may contain a solvent as discussed above. As another example, a stream containing additional $C_n$ alcohol equivalents, $C_{n+1}$ alcohol equivalents or both may be combined with the crude reductive carbonylation product or portion thereof or fed separately to the Guerbet reaction zone. For example in some embodiments in which n=1, reactants such as methanol, acetaldehyde, ethanol or the dimethyl acetal of acetaldehyde may be fed together with or separately from the crude reductive carbonylation product or portion thereof. In some embodiments, water or hydrogen is present.

The Guerbet reaction produces a product composition containing the product compound having the structure of formula IV described above. Because Q in formula IV is either an alcohol or aldehyde group having one carbon, the product compound may be an alcohol, and aldehyde, or a blend of both an alcohol and an aldehyde. Thus, in embodiments in which n=1, the product compound includes isobutanol, isobutyraldehyde, or both compounds. In embodiments in which n=2, the product compound includes 2-methylbutyraldehyde, 2-methyl-1-butanol, or both compounds. In embodiments in which n=3, the product compound includes 2-ethylpentanal, and 2-ethyl-1-pentanol, or both compounds. As discussed above, the relative amounts of alcohol and aldehyde compounds in the product compound can be altered by varying the identity of the Guerbet catalyst and other reaction parameters depending on the desired product mix. Thus, in some embodiments, the product composition comprises at least about 0.5 moles in which Q is an aldehyde group having one carbon for every mole of product compound in which Q is an alcohol group having one carbon. In some embodiments, the product composition comprises at least about 1.0, at least about 2.0, at least about 3.0, at least about 4.0, at least about 5.0, at least about 7.5, at least about 10.0, at least about 12.5, or at least about 15.0 moles of product compound in which Q is an aldehyde group having one carbon for every mole of product compound in which Q is an alcohol group having one carbon. Similarly, in some embodiments, the product composition comprises at least about 1.0, at least about 2.0, at least about 3.0, at least about 4.0, at least about 5.0, at least about 7.5, at least about 10.0, at least about 12.5, or at least about 15.0 moles of product compound in which Q is an alcohol group having one carbon for every mole of product compound in which Q is an aldehyde group having one carbon. The ratio of product compounds in which Q is an aldehyde having one carbon to product compounds in which Q is an alcohol having one carbon (aldehyde:alcohol) can also be expressed as a range. Thus, embodiments exist in which this ratio (aldehyde:alcohol) is from 0.05:1 to 20:1, from 0.05:1 to 0.10:1, from 0.05:1 to 1:1, from 0.1:1 to 0.5:1, from 0.1:1 to 1:1, from 0.5:1 to 1:1, from 1:1 to 20:1, from 1:1 to 5:1, from 1:1 to 10:1, from 1:1 to 15:1, from 5:1 to 10:1, from 10:1 to 20:1, from 15:1 to 20:1, from 10:1 to 15:1.

Additional Processing

The invention may include other process steps to process the product composition. For example, the product composition may be subjected to one or more separation processes to concentrate or to separate various components. Some examples include separation processes such as evaporation, distillation, phase separation, decanting, extraction, membrane separation, or combinations of two or more of the following. In some embodiments, the separation processes allow concentrations of one or more $C_n$ alcohol equivalents and $C_{n+1}$ alcohol equivalents from the product compositions for recycling to earlier in the process so that they may be contacted with the Guerbet catalyst again.

Listing of Non-Limiting Embodiments

The invention provides processes comprising:

(a) contacting hydrogen, carbon monoxide, and a primary alkyl alcohol having n carbon atoms in the presence of a carbonylation catalyst to form a crude reductive carbonylation product comprising at least one $C_{n+1}$ alcohol equivalent having (n+1) carbon atoms and at least one $C_n$ alcohol equivalent having n carbon atoms, wherein the reductive carbonylation catalyst comprises a complex of cobalt, iodide, and an onium cation or an alkali metal cation of the general formula $Y_2CoI_4$, wherein Y is the onium cation or the alkali metal cation;

(b) contacting at least one $C_{n+1}$ alcohol equivalent and at least one $C_n$ alcohol equivalent with a Guerbet catalyst to form a product composition comprising at least one product molecule, wherein:

n is selected from 1, 2 or 3;

the total number of moles of the at least one $C_n$ alcohol equivalent contacted with the Guerbet catalyst is at least equal to the number of moles one $C_{n+1}$ alcohol equivalent contacted with the Guerbet catalyst and, if n=1, is equal to at least 2.0 multiplied by the number of moles one $C_{n+1}$ alcohol equivalent contacted with the Guerbet catalyst;

contacting the at least one $C_n$ alcohol equivalent and the at least one $C_{n+1}$ alcohol equivalent with the Guerbet catalyst comprises contacting the crude reductive carbonylation product or a portion thereof with the Guerbet catalyst; and the at least one product molecule has the structure of formula IV:

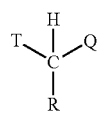

IV wherein:

C is a carbon atom;

H is a hydrogen atom;

Q is an alcohol or aldehyde group having one carbon;

R is a linear alkyl group having n carbon atoms; and

T is an alkyl group having (n−1) carbon atoms, except that when n=1,

T is methyl.

The invention further provides processes comprising contacting at least one $C_n$ alcohol equivalent having n carbon atoms and at least one $C_{n+1}$ alcohol equivalent having (n+1) carbon atoms with a Guerbet catalyst to form a product composition comprising at least one product molecule, wherein:

the total number of moles of the at least one $C_n$ alcohol equivalent contacted with the Guerbet catalyst is at least equal to the number of moles one $C_{n+1}$ alcohol equivalent contacted with the Guerbet catalyst and, if n=1, is equal to at least 2.0 multiplied by the number of moles one $C_{n+1}$ alcohol equivalent contacted with the Guerbet catalyst;

n=1, 2 or 3;

at least some of the at least one $C_n$ alcohol equivalent and at least some of the least one $C_{n+1}$ alcohol equivalent are within or derived from a crude reductive carbonylation product, the crude reductive carbonylation product being a product of contacting hydrogen, carbon monoxide, and a primary alkyl alcohol having n carbon atoms in the presence of a reductive carbonylation catalyst, the reductive carbonylation catalyst comprising a complex of cobalt, iodide, and an onium cation or an alkali metal cation of the general formula $Y_2CoI_4$, wherein Y is the onium cation or the alkali metal cation; and the at least one product molecule has the structure of formula IV, above.

The invention further provides embodiments of each of the processes described in each of the above paragraphs, including various embodiments having each of the features, ranges and combinations of features and ranges described in those paragraphs, wherein the total number of moles of $C_n$ alcohol equivalents in the crude reductive carbonylation product is at least equal to the total number of moles of $C_{n+1}$ alcohol equivalents in the crude reductive carbonylation product and, if n=1, is equal to at least 2.0 multiplied by the total number of moles of $C_{n+1}$ alcohol equivalent in the crude reductive carbonylation product.

The invention further provides embodiments of each of the processes described in each of the above paragraphs, including various embodiments having each of the features, ranges and combinations of features and ranges described in those paragraphs, wherein contacting the at least one $C_{n+1}$ alcohol equivalent and at least one $C_n$ alcohol equivalent with the Guerbet catalyst comprises contacting at least some supplemental $C_n$ alcohol equivalent with the Guerbet catalyst.

The invention further provides embodiments of each of the processes described in each of the above paragraphs, including various embodiments having each of the features, ranges and combinations of features and ranges described in those paragraphs, wherein the crude reductive carbonylation product or portion thereof that is contacted with the Guerbet catalyst comprises a dialkyl acetal of an aldehyde, the aldehyde being a linear alkyl aldehyde having (n+1) carbon atoms, and the dialkyl acetal comprising two linear alkoxy groups having n carbon atoms. The invention further provides embodiments of each of the processes and embodiments described in this paragraph, including various embodiments having each of the features, ranges and combinations of features and ranges described in this paragraph, in which the dialkyl acetal of the linear alkyl aldehyde comprises at least about 30, at least about 20, at least about 25, at least about 40, at least about 50, at least about 60, at least about 70, at least about 80, at least about 90, from 20 to 99, from 20 to 95, from 30 to 99, from 50 to 99, from 20 to 50, from 50 to 60, from 60 to 70, from 70 to 80, from 80 to 90, from 90 to 99, from 80 to 99, from 70 to 99 or from 60 to 99 molar percent of the total number of $C_{n+1}$ alcohol equivalents present in the crude reductive carbonylation product (or portion thereof) that is contacted with the Guerbet catalyst. The invention further provides embodiments of each of the processes and embodiments described in this paragraph, including various embodiments having each of the features, ranges and combinations of features and ranges described in this paragraph, in which alkoxy groups on the dialkyl acetal of the linear alkyl aldehyde comprise at least about 5, at least about 10, at least about 15, at least about 20, at least about 25, at least about 30, at least about 40, at least about 50, at least about 60, at least about 70, at least bout 80, at least about 90, from 5 to 25, from 5 to 10, from 5 to 15, from 5 to 20, from 5 to 25, from 10 to 20, from 10 to 25, from 10 to 30, from 10 to 40, from 10 to 50, from 10 to 60, from 20 to 50, from 20 to 30, from 30 to 40, from 40 to 50, from 50 to 60, from 60 to 70, from 70 to 80, from 80 to 90, from 80 to 95, from 90 to 99 or from 10 to 99 molar percent of all $C_n$ alcohol equivalents present in the crude reductive carbonylation product (or portion thereof) that is contacted with the Guerbet catalyst.

The invention further provides embodiments of each of the processes described in each of the above paragraphs, including various embodiments having each of the features, ranges and combinations of features and ranges described in those paragraphs, wherein the process further comprises separating at least some of the crude reductive carbonylation product from the reductive carbonylation catalyst by vaporization prior to contacting the at least one $C_n$ alcohol equivalent and the at least one $C_{n+1}$ alcohol equivalent with the Guerbet catalyst.

The invention further provides embodiments of each of the processes described in each of the above paragraphs, including various embodiments having each of the features, ranges and combinations of features and ranges described in those paragraphs, wherein, during the contacting of contacting hydrogen, carbon monoxide, and a primary alkyl alcohol having n carbon atoms in the presence of a reductive carbonylation catalyst, the reductive carbonylation catalyst is present in an amount ranging from 0.001 moles to 10 moles of the catalyst per 100 moles of the primary alkyl alcohol having n carbon atoms; or from 0.01 moles to 5 moles of catalyst per 100 moles of primary alkyl alcohol having n carbon atoms, or from 0.02 moles to 5 moles of catalyst per 100 moles of primary alkyl alcohol having n carbon atoms.

The invention further provides embodiments of each of the processes described in each of the above paragraphs, including various embodiments having each of the features, ranges and combinations of features and ranges described in those paragraphs, wherein the onium cation is of the general formula (I) or (II)

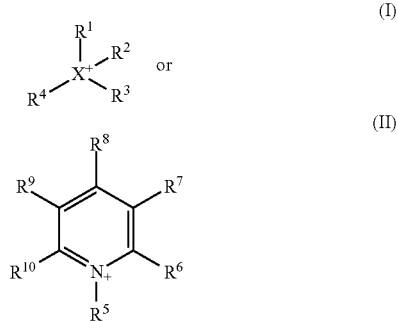

For formula (I), X can be phosphorus (P) or nitrogen (N) and $R^1$ is methyl. $R^2$, $R^3$, and $R^4$ are independently selected from alkyl having up to 12 carbon atoms and aryl. When $R^2$, $R^3$, and/or $R^4$ are aryl, each aryl is the same, and can be phenyl, tolyl, xylyl, or mesityl. For formula (II), $R^5$ is methyl and $R^6$, $R^7$, $R^8$, $R^9$, and $R^{10}$ are hydrogen. The crude reductive carbonylation product comprises less than 1 weight percent of methyl iodide.

The invention further provides embodiments of each of the processes described in each of the above paragraphs, including various embodiments having each of the features, ranges and combinations of features and ranges described in those paragraphs, wherein the onium cation is formula (I), X is phosphorus (P), $R^1$ is methyl and $R^2$, $R^3$, and $R^4$ are independently selected from alkyl having up to 12 carbon atoms and aryl, wherein when $R^2$, $R^3$, and/or $R^4$ are aryl, each aryl is the same, and can be phenyl, tolyl, xylyl, or mesityl: or the onium cation is formula (II), $R^5$ is methyl and $R^6$, $R^7$, $R^8$, $R^9$, and $R^{10}$ are hydrogen: or the onium cation is selected from the group consisting of methyltriphenylphosphonium, methyltributylphosphonium, methyltrioctylphosphonium, and 1-methylpyridinium: or the onium cation is selected from the group consisting of methyltriphenylphosphonium and 1-methylpyridinium: or the onium cation comprises methyltriphenylphosphonium: or the alkali metal cation is selected from the group consisting of lithium, sodium, potassium, rubidium, and cesium: or the alkali metal cation is selected from the group consisting of lithium, sodium, potassium: or the catalyst is selected from the group consisting of bis(methyltriphenylphosphonium) cobalt tetraiodide, bis(methyltributylphosphonium) cobalt tetraiodide, bis(methyltrioctylphosphonium), and bis(1-methylpyridinium) cobalt tetraiodide.

The invention further provides embodiments of each of the processes described in each of the above paragraphs, including various embodiments having each of the features, ranges and combinations of features and ranges described in those paragraphs, wherein, during the contacting of hydrogen, carbon monoxide, and a primary alkyl alcohol having n carbon atoms in the presence of a reductive carbonylation catalyst, cobalt is present in an amount ranging from 0.001 moles to 10 moles of the cobalt per 100 moles of the primary alkyl alcohol having n carbon atoms, or from 0.01 moles to 5 moles of cobalt per 100 moles of the primary alkyl alcohol having n carbon atoms, or from 0.02 moles to 5 moles of cobalt per 100 moles of the primary alkyl alcohol having n carbon atoms.

The invention further provides embodiments of each of the processes described in each of the above paragraphs, including various embodiments having each of the features, ranges and combinations of features and ranges described in those paragraphs, wherein the reductive carbonylation catalyst further comprises a phosphine ligand of the general formula

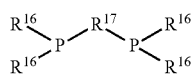

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 22 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms. The invention provides embodiments of each of the processes and embodiments described in this paragraph, including various embodiments having each of the features, ranges and combinations of features and ranges described in this paragraph, in which the phosphine ligand is selected from the group consisting of 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and 1,3-bis(diphenylphosphino)cyclobutane: or the phosphine ligand is selected from the group consisting of 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1,-tris(diphenylphosphinomethyl)ethane; and 1,1,1-tris(diethylphosphinomethyl)ethane: or the phosphine ligand is selected from the group consisting of 1,3-bis(diphenylphosphino)propane; 1,1,1,-tris(diphenylphosphinomethyl)ethane; and 1,1,1-tris(diethylphosphinomethyl)ethane: or the phosphine ligand comprises 1,3-bis(diphenylphosphino)propane. The invention provides embodiments of each of the processes and embodiments described in this paragraph, including various embodiments having each of the features, ranges and combinations of features and ranges described in this paragraph, in which the phosphine ligand is of the general formula

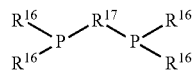

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 22 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms. The crude reductive carbonylation product comprises less than 1 weight percent of methyl iodide. The invention further provides embodiments of each of the processes and embodiments described in this paragraph, including various embodiments having each of the features, ranges and combinations of features and ranges described in this paragraph, in which the ratio phosphine ligand to cobalt present in the reductive carbonylation catalyst (phosphine ligand:cobalt) ranges from 0.025:1 to 2:1 or ranges from 0.025:1 to 1:1.

The invention further provides embodiments of each of the processes described in each of the above paragraphs, including various embodiments having each of the features, ranges and combinations of features and ranges described in those paragraphs, wherein the contacting of hydrogen, carbon monoxide, and a primary alkyl alcohol having n carbon atoms in the presence of a reductive carbonylation catalyst occurs in the presence of a solvent selected from the group consisting of alkanes and arenes having 6 to 20 carbon atoms, ketones having 5 to 20 carbon atoms, esters having 5 to 20 carbon atoms, ethers having 5 to 20 carbon atoms, and alkyl carbonate esters having 3 to 20 carbon atoms: or wherein the contacting further occurs in the presence of a solvent selected from the group consisting of toluene, heptane, cyclohexane, ethylbenzene, diethyl ether, and 4-methylanisole.

The invention further provides embodiments of each of the processes described in each of the above paragraphs, including various embodiments having each of the features, ranges and combinations of features and ranges described in those paragraphs, wherein the reductive carbonylation catalyst further comprises a phosphonium iodide. The invention further provides embodiments of each of the processes and embodiments described in this paragraph, including various embodiments having each of the features, ranges and combinations of features and ranges described in this paragraph, in which the phosphonium iodide is selected from the group consisting of methyltriphenylphosphonium iodide, methyltributylphosphonium iodide, methyltrioctylphosphonium iodide, butyltridodecylphosphonium iodide, tetraoctylphosphonium iodide, tetrabutylphosphonium iodide, triphenyl(hexyl)phosphonium iodide, triphenyl(octyl)phosphonium iodide, tribenzyl(octyl)phosphonium iodide, tribenzyl(dodecyl)phosphonium iodide, triphenyl(decyl)phosphonium iodide, triphenyl(dodecyl)phosphonium iodide, tetra (2-methylpropyl)phosphonium iodide, tris(2-methylpropyl)-(butyl)phosphonium iodide, triphenyl(3,3-dimethylbutyl)phosphonium iodide, triphenyl(3-methylbutyl)phosphonium iodide, tris(2-methylbutyl)(3-methyl-butyl)phosphonium iodide, triphenyl[2-trimethylsilylethyl]phosphonium iodide, tris(p-chlorophenyl)(dodecyl)phosphonium iodide, hexyltris(2,4,6-trimethylphenyl)phosphonium iodide, tetradecyltris(2,4,6-trimethyl-phenyl)phosphonium iodide, dodecyltris(2,4,6-trimethylphenyl)phosphonium iodide, methyltrioctylphosphonium iodide, methyltributylphosphonium iodide, and methyltricyclohexylphosphonium iodide: or methyltriphenylphosphonium iodide, methyltributylphosphonium iodide, and methyltrioctylphosphonium iodide: or comprises methyltriphenylphosphonium iodide. The invention further provides embodiments of each of the processes and embodiments described in this paragraph, including various embodiments having each of the features, ranges and combinations of features and ranges described in this paragraph, wherein the molar ratio of phosphonium iodide to cobalt (phosphonium iodide:cobalt) ranges from 1:1 to 50:1 or ranges from 1:1 to 20:1

The invention further provides embodiments of each of the processes described in each of the above paragraphs, including various embodiments having each of the features, ranges and combinations of features and ranges described in those paragraphs, wherein the crude reductive carbonylation product comprises less than 1 weight percent of methyl iodide, less than 0.8 weight percent, less than 0.5 weight percent, less than 0.1 weight percent, less than 0.05 weight percent, less than 100 ppm, less than 50 ppm, less than 10 ppm, less than 100 ppb, less than 50 ppb, or less than 10 ppb of methyl iodide, based on the total weight of the crude reductive carbonylation product based on the total weight of said crude reductive carbonylation product.

The invention further provides embodiments of each of the processes described in each of the above paragraphs, including various embodiments having each of the features, ranges and combinations of features and ranges described in those paragraphs, wherein the process is carried out at a temperature ranging from 100° C. to 250° C.; or from 150° C. to 230° C.

The invention further provides embodiments of each of the processes described in each of the above paragraphs, including various embodiments having each of the features, ranges and combinations of features and ranges described in those paragraphs, wherein the process is carried out at a pressure ranging from 100 kPa (15 psig) to 60 MPa (8700 psig); or from 1 MPa (150 psig) to 40 MPa (5800 psig); or from 6.9 MPa (1000 psig) to 34 MPa (4900 psig).

The invention further provides embodiments of each of the processes described in each of the above paragraphs, including various embodiments having each of the features, ranges and combinations of features and ranges described in those paragraphs, wherein the molar ratio of carbon monoxide to hydrogen, $CO:H_2$, ranges from 10:1 to 1:10 or from 5:1 to 1:5.

The invention further provides processes comprising contacting at least one dialkyl acetal compound with a Guerbet catalyst to form a product composition comprising at least one product molecule, wherein the dialkyl acetal compound is the dialkyl of a linear alkyl aldehyde having (n+1) carbon atoms, and the dialkyl acetal comprises two linear alkoxy groups having n carbon atoms, and n=1, 2 or 3, and the at least one product molecule has the structure of formula IV, above. The invention provides embodiments of each of the processes described in this paragraph in which contacting of the at least one dialkyl acetal compound with the Guerbet catalyst occurs in the presence of water. The invention further provides embodiments of each of the processes and embodiments described in this paragraph, including various embodiments having each of the features, ranges and combinations of features and ranges described in this paragraph, in which contacting the dialkyl acetal with the Guerbet catalyst comprises contacting at least some supplemental $C_n$ alcohol equivalent having n carbon atoms with the Guerbet catalyst The invention further provides embodiments of each of the processes described in each of the above paragraphs, including various embodiments having each of the features, ranges and combinations of features and ranges described in those paragraphs, wherein n is 1, n is 2, n is 3, n is 1 or 2, n is 1 or 3, or n is 2 or 3.

The invention further provides embodiments of each of the processes described in each of the above paragraphs, including various embodiments having each of the features, ranges and combinations of features and ranges described in those paragraphs, wherein ratio of product compounds in which Q is an aldehyde having one carbon to product compounds in which Q is an alcohol having one carbon (aldehyde:alcohol) from 0.05:1 to 20:1, from 0.05:1 to 0.10:1, from 0.05:1 to 1:1, from 0.1:1 to 0.5:1, from 0.1:1 to 1:1, from 0.5:1 to 1:1, from 1:1 to 20:1, from 1:1 to 5:1, from 1:1 to 10:1, from 1:1 to 15:1, from 5:1 to 10:1, from 10:1 to 20:1, from 15:1 to 20:1 or from 10:1 to 15:1.

The invention further provides embodiments of each of the processes described in each of the above paragraphs, including various embodiments having each of the features, ranges and combinations of features and ranges described in those paragraphs, wherein the Guerbet catalyst is in a solid phase when it is contacted with the at least one $C_n$ alcohol equivalent and the at least one $C_n$ alcohol equivalent. The invention further provides embodiments of each of the processes and embodiments described in this paragraph, including various embodiments having each of the features, ranges and combinations of features and ranges described in this paragraph, in which the Guerbet catalyst comprises a material selected from heterogeneous vanadium oxide supported on titania, palladium oxide supported on titania, or copper oxide-zinc oxide supported on alumina.

The invention further provides embodiments of each of the processes described in each of the above paragraphs, including various embodiments having each of the features, ranges and combinations of features and ranges described in those paragraphs, wherein the Guerbet catalyst is in a liquid phase when it is contacted with the at least one $C_n$ alcohol equivalent and the at least one $C_n$ alcohol equivalent. The invention further provides embodiments of each of the processes and embodiments described in this paragraph, including various embodiments having each of the features, ranges and combinations of features and ranges described in this paragraph, in which the Guerbet catalyst comprises a material selected from [IrCl(cod)]$_2$, [Cp*IrCl$_2$]$_2$, [Ir(OH)(cod)]$_2$, IrCl(PPh$_3$)$_3$, IrCl$_3$(3H$_2$O), RhCl$_3$/PBu$_3$, [RuCl(eta6-p-cymene)]Cl, PdCl$_2$ and RuCl$_2$.

The invention has been described in detail with particular reference to certain embodiments thereof, but it will be understood that variations and modifications can be effected within the spirit and scope of the invention. The forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention. The inventors hereby state their intent to rely on the Doctrine of Equivalents to determine and assess the reasonably fair scope of the present invention as pertains to any apparatus not materially departing from but outside the literal scope of the invention as set forth in the following claims. Unless otherwise indicated, all percentages are by weight.

EXAMPLES

The phosphonium salts and ammonium salts used in these examples are easily prepared by alkylation of the parent tertiary phosphine or amine with an alkyl halide, a process well known to practitioners of the art. Complexes of the type Y$_2$CoI$_4$ where Y=MePPh$_3$ (methyltriphenylphosphonium) and where Y=PyMe (1-methylpyridinium), were prepared by the method of Wegman et al., *J. Mol. Cat.*, 32, (1985), 125-136.

Solvents and alcohols were purchased and used without further processing.

STY=space-time-yield.

DMA=dimethyl acetal of acetaldehyde dppp=1,3-bis(diphenyl phosphino)propane

Co(OAc)$_2$ 4H$_2$0=cobalt acetate tetrahydrate

PPh$_3$=triphenylphosphine

Example 1

A crude reductive carbonylation product useful in isobutyraldehyde synthesis was prepared from methanol and syngas via six separate methanol reductive carbonylation reactions. In each reaction about 2.186 g (0.00185 moles) of the bis(methyltriphenylphosphonium)cobalt tetraiodide complex was dissolved in 75 mL of methanol (1.85 moles) and charged to a 100 mL Hastelloy autoclave. The autoclave was sealed and purged three times with nitrogen then pressurized to 69 bar (1000 psig) with 1:1 CO:H$_2$ and heated to 190° C. Upon reaching the desired temperature, the reactor was pressurized to a total pressure of 138 bar (2000 psig) with 1:1 CO:H$_2$. After one hour the reactor was cooled to room temperature, vented and the product decanted.

The product solutions from all six autoclave reactions were combined in a 1 L round bottom flask equipped with a 20 cm vigreux column that was connected to a water-cooled short path distillation apparatus. The distillation apparatus was connected to a vacuum source and a 500 mL receiving flask cooled with dry ice and acetone. The crude reductive carbonylation product was then separated from the cobalt catalyst by placing the distillation apparatus under a pressure of 90 to 92 torr and heating the distillation flask with an oil bath to 90° C. After three hours under these conditions 253 g of a clear liquid was collected in the receiving flask and the composition analyzed by gas chromatography (GC). This composition was used as the feed material for Examples 1 through 7.

The GC analytical method entailed the following: samples were weighed into a GC vial to a recorded weight of 0.1 gram with an accuracy of five significant figures. Initially a stock ISTD solution comprising 75 g of cyclohexanone in acetonitrile was made-up. To 1.0 gram (with an accuracy of three significant figures) of the reaction product, approximately 7.86 gram (with an accuracy of five significant figures) of ISTD solution was added. The vial was then capped and gently mixed. The contents were then transferred into a 2 mL GC vial. The vials were then placed on a heat plate at 80° C. for 30 minutes. To separate all components, each sample was injected on two columns running in parallel on one instrument, a Shimadzu 2010 gas chromatograph with an AOC-20 autosampler. The weight percent concentration of analytes was detected using this approach using the TCD and FID detectors. The composition of the distillate generated in this example is summarized in Table 4.

TABLE 4

Composition of distilled methanol reductive carbonylation product.

|  | Acetaldehyde | Water | Acetaldehyde Dimethyl Acetal | Methyl Acetate | Methanol | Ethanol | Crotonaldehyde |
|---|---|---|---|---|---|---|---|
| Wt. % | 0.69% | 3.44% | 18.75% | 3.32% | 72.32% | 0.1% | 0.86% |
| mmoles | 39.6 | 483.0 | 526.4 | 113.4 | 5710.7 | 5.5 | 31.0 |

MeOH equiv. = 6879 mmol
EtOH equiv. = 571 mmol
MeOH equiv./EtOH equiv. = 12

The distillate in this example was used as liquid feed material for a heterogeneously catalyzed fixed bed vapor phase Guerbet reaction. The heterogeneous catalyst charge used in this example consisted of 2.32 g (2.5 mL) of an anatase ($TiO_2$) support impregnated with 27 wt. % vanadium oxide ($V_2O_5$). The catalyst was prepared by spraying 100 g of the anatase rods (Aerolyst 7708 obtained from Evonik Industries) twenty times with about 44 g each time of a 3.8 wt. % aqueous solution of vanadyl oxalate (prepared from a 2:1 molar mixture of oxalic acid and ammonium metavanadate). The rods were dried at 200° C. in air for two hours between each impregnation then calcined at 500° C. for two hours in a muffle furnace in air after the final impregnation.

The reactor used in this example, an H.E.L. FlowCAT system, is a computer controlled continuous flow tubular stainless steel reactor system that allows both gas and liquid feeds to pass through a heated catalyst bed. The catalyst was charged to the center of the reactor tube by filling the base of the reactor with the appropriate amount of 1 mm diameter glass beads so that the center of the catalyst bed is positioned in the middle of the reactor. The catalyst was then added followed by more glass beads up to the top of the reactor tube. Liquid and gas feeds were supplied to the top of the reactor via pumps then passed through the catalyst bed and the base of the reactor. The reactor effluent flowed to the sample system and collected directly in a collection vial chilled in a dry ice bath.

The FlowCAT allows the user to configure a plan tailored to desired reaction conditions. For the experiment described in this example the plan included four steps: Step 1 included a temperature set point at 350° C. which was controlled by the reactor jacket temperature and a nitrogen flow set point of 80 mL/minute. Once the temperature was within 2° C. of the desired set point, the plan automatically advanced to step 2. This step was programmed with the same conditions as step 1, but included the introduction of liquid feed at a set point of 0.2 mL/minute. This step was held for twenty minutes to allow for the catalyst system to re-equilibrate if there were any exothermic conditions during the initial delivery of liquid feed onto the catalyst. At the end of the twenty minute hold the collection vial was replaced with a fresh vial and the plan continued to step 3. All set points were the same in this step as step 2 but with the hold time set to 100 minutes so total feed between steps 2 and 3 was 20 milliliters. The final step (Step 4) was identical to step 1 (no liquid feed) but with the hold time set to thirty minutes. When the plan had finished the collection vial was removed, weighed and the product analyzed by GC using the procedures describe above. Weight percent product composition is summarized in Table 5. The production rate or space-time-yield (STY) of the combined millimoles of isobutyraldehyde and isobutanol are summarized in Table 6.

This example clearly demonstrates that iso-butyraldehyde can indeed be produced from the effluent of a cobalt catalyzed methanol reductive carbonylation reaction and that the dimethyl acetal of acetaldehyde (DMA) may be consumed in a Guerbet reaction to make iso-butyraldehyde. The concentration of DMA in the reductive carbonylation product was originally 18.75% but was reduced to 0.88% upon exposure to the 27% $V_2O_5/TiO_2$ catalyst at 350° C. The resulting product contained isobutyraldehyde in 2.83 wt % concentration and isobutanol in 0.45 wt % concentration, which equates to a STY of 1,480 mmol (iHBu+iHBuOH)/L cat./hr.

Example 2

Example 1 was repeated except that the 27% $V_2O_5/TiO_2$ catalyst was first regenerated at 395° C. with a stream of 100 mL/min nitrogen and 50 mL/min air for one hour to remove coke deposits. The isobutyraldehyde synthesis reaction was then carried out at 325° C. instead of 350° C. The weight percent product composition is summarized in Table 5. The space-time-yield of the combined millimoles of isobutyraldehyde and isobutanol is summarized in Table 6. This example shows that isobutyraldehdye and isobutanol are formed in lower amount (0.76 wt %, 0.21 wt %, 466 STY) at the lower reaction temperature. Consistent with this observation is the fact that the DMA conversion is lower with 3.92% of unreacted DMA remaining in the product.

Example 3

Example 2 was repeated except that the reaction was carried out at 300° C. instead of 325° C. The weight percent product composition is summarized in Table 5. The combined space-time-yield of the millimoles of isobutyraldehyde and isobutanol is summarized in Table 6. This example indicates that isobutyraldehyde and isobutanol are formed in lower amount (0.12 wt %, 0.09 wt % 103 STY) when the temperature is lowered further. Consistent with this observation is the fact that the DMA conversion is lower with 10.42 wt % of unreacted DMA remaining in the product.

Example 4

Example 1 was repeated except that 2.02 g (8.6 mL) of copper-zinc oxide on alumina ($CuO$—$ZnO/Al_2O_3$) catalyst was used and the nitrogen flow rate was 40 mL/min.

The catalyst was prepared via the following procedure, which is a modification of Reddy, B. M.; Reddy, E. P.; Manohar, B. J. Chem. Soc., Chem. Commun., 997-998, 1992. To a 5 L flask was added 150.0 g of urea and 2 L of deionized water; the pH of this solution was about 5, as determined with pH paper. 49.67 g of zinc nitrate hexahydrate and 17.56 g of copper nitrate trihydrate were dissolved in the solution, then 20.0 g of gamma alumina (Alfa Aesar #44757) suspended in the resulting pale blue solution. The mixture was then heated to 98° C. for 3 hours, during which time the pH rose to about neutral. The mixture was then cooled to room temperature and the pale blue solid was isolated on a glass frit and washed with deionized water (2 L) and air dried for 5 hours under pull of vacuum. The light blue cake was then dried in a muffle furnace at 110° C. for 16 hours then sieved to 8×14 mesh and calcined at 450° C. in air in the muffle furnace for 20 hours to give dark gray particles.

Reaction procedures were the same as Example 1. The weight percent composition of the product from this reaction is summarized in Table 5. The space-time-yield of the combined millimoles of isobutyraldehyde and isobutanol is summarized in Table 6. This example shows that the copper based catalyst can produce isobutyraldehyde and isobutanol in 2.56 wt % and 3.34 wt % concentration from the methanol reductive carbonylation effluent but in lower rate (122 STY) than observed with the vanadium based catalyst used in Example 1.

Example 5

Example 4 was repeated except that the CuO—ZnO/$Al_2O_3$ catalyst was first regenerated at 395° C. with a stream of 100 mL/min nitrogen and 50 mL/min air for one hour. The iso-butyraldehyde synthesis reaction was then carried out at 325° C. instead of 350° C. The weight percent product composition is summarized in Table 5. The space-time-yield of the combined millimoles of isobutyraldehyde and isobutanol is summarized in Table 6. This example shows that isobutyraldehyde and isobutanol are formed in 1.39 wt % and 1.24 wt % concentration and at a higher rate (182 STY) observed using the higher temperature in Example 4.

Example 6

Example 1 was repeated using 2.08 g (2.2 mL) of 1 wt. % palladium on titania (Pd/$TiO_2$) catalyst was used and the nitrogen flow rate was 40 mL/min. The catalyst was prepared by the wetness impregnation method. Palladium acetate (0.22 g) was dissolved in 6 g of acetone and stirred for 10 minutes to completely dissolve the salt. This solution was immediately added to $TiO_2$ powder (Saint Gobain-Norpro, Dms2011-0416, 10 g) in a single neck round bottom flask. For effective impregnation, the flask was shaken for 30 seconds. The solvent was removed by evaporation with a rotovap set at 80° C. for 30 minutes and the resulting material reduced by 10% hydrogen (20 mL/min) in helium (180 mL/min) at 300° C. for 2 hours at a ramp rate of 5° C./min.

The weight percent composition of the product from this reaction is summarized in Table 5. The space-time-yield of the combined millimoles of isobutyraldehyde and isobutanol is summarized in Table 6. This example shows that the Pd/$TiO_2$ catalyst can also produce isobutyraldehyde and isobutanol from the methanol reductive carbonylation effluent. The isobutyraldehyde was formed in 1.0 wt % concentration and the isobutanol in 0.66 wt % concentration giving a STY of 341 mmol (iHBu+iHBuOH)/L cat./hr.

Example 7

Example 6 was repeated except that the Pd/$TiO_2$ catalyst was first regenerated at 395° C. with a stream of 100 mL/min nitrogen and 50 mL/min air for one hour and the iso-butyraldehyde synthesis reaction was then carried out at 325° C. instead of 350° C. The weight percent product composition is summarized in Table 5. The space-time-yield of the combined millimoles of isobutyraldehyde and isobutanol is summarized in Table 6. This example shows that isobutyraldehyde and isobutanol are formed in 1.59 wt % and 0.9 wt % concentration and at more than twice the rate (841 STY) observed using the higher temperature in Example 6.

TABLE 5

Weight percent composition of the products obtained from conversion of methanol reductive carbonylation distillate over heterogeneous mixed oxide catalysts.

| Ex. | Water (wt %) | HAc (wt %) | MeOH (wt %) | EtOH (wt %) | Acrolein (wt %) | HPr (wt %) | iHBu (wt %) | Methacrolein (wt %) | DMA (wt %) | n-HBu (wt %) | MeOAc (wt %) | iBuOH (wt %) | HCr (wt %) | nBuOH (wt %) |
|---|---|---|---|---|---|---|---|---|---|---|---|---|---|---|
| 1 | 13.97 | 3.30 | 69.46 | 1.05 | 1.00 | 0.71 | 2.83 | 1.25 | 0.88 | 4.68 | 0.00 | 0.45 | 0.43 | 0.00 |
| 2 | 6.54 | 2.87 | 80.18 | 1.42 | 0.76 | 0.41 | 0.76 | 0.64 | 3.92 | 2.01 | 0.00 | 0.21 | 0.28 | 0.00 |
| 3 | 4.81 | 1.81 | 79.54 | 1.40 | 0.34 | 0.13 | 0.12 | 0.22 | 10.42 | 0.89 | 0.00 | 0.09 | 0.23 | 0.00 |
| 4 | 0.00 | 0.17 | 85.66 | 0.57 | 0.00 | 0.00 | 2.56 | 0.00 | 1.66 | 0.00 | 5.95 | 3.34 | 0.00 | 0.08 |
| 5 | 0.00 | 0.11 | 90.74 | 0.23 | 0.00 | 0.00 | 1.39 | 0.00 | 2.04 | 0.00 | 4.25 | 1.24 | 0.00 | 0.00 |
| 6 | 82.18 | 0.00 | 15.57 | 0.20 | 0.00 | 0.00 | 1.00 | 0.00 | 0.00 | 0.00 | 0.33 | 0.66 | 0.00 | 0.06 |
| 7 | 29.28 | 0.89 | 64.65 | 0.74 | 0.00 | 0.00 | 1.59 | 0.00 | 0.00 | 0.00 | 1.84 | 0.90 | 0.00 | 0.11 |

Abbreviation definitions:

HAc = acetaldehyde, MeOH = methanol, EtOH = ethanol, HPr = propionaldehyde, iHBu = isobutyraldehyde, DMA = dimethylacetal of acetaldehyde, iBuOH = isobutanol, HCr = crotonaldehyde, nBuOH = n-butanol.

TABLE 6

Space-time-yield (STY) of isobutyraldehyde and isobutanol formed from conversion of methanol reductive carbonylation distillate over heterogeneous mixed oxide catalysts.

| Example | Reactor Conditions | Catalyst Description | STY (mmole iHBu + iHBuOH/ Liter cat/h) |
|---|---|---|---|
| 1 | 350° C., 80 mL/min N2, 0.2 mL/min LFR | 27% $V_2O_5$/$TiO_2$ | 1,480 |
| 2 | 325° C., 80 mL/min N2, 0.2 mL/min LFR | 27% $V_2O_5$/$TiO_2$ | 466 |
| 3 | 300° C., 80 mL/min N2, 0.2 mL/min LFR | 27% $V_2O_5$/$TiO_2$ | 103 |
| 4 | 350° C., 40 mL/min N2, 0.2 mL/min LFR | CuO—ZnO/$Al_2O_3$ | 122 |
| 5 | 325° C., 40 mL/min N2, 0.2 mL/min LFR | CuO—ZnO/$Al_2O_3$ | 182 |

TABLE 6-continued

Space-time-yield (STY) of isobutyraldehyde and isobutanol formed from conversion of methanol reductive carbonylation distillate over heterogeneous mixed oxide catalysts.

| Example | Reactor Conditions | Catalyst Description | STY (mmole iHBu + iHBuOH/ Liter cat/h) |
|---|---|---|---|
| 6 | 350° C., 40 mL/min N2, 0.2 mL/min LFR | 1% Pd/TiO$_2$ | 341 |
| 7 | 325° C., 40 mL/min N2, 0.2 mL/min LFR | 1% Pd/TiO$_2$ | 842 |

LFR = liquid feed rate of the distillate.

Demonstration of DMA as a Feed.

Examples 8-10 encompass a series of fixed bed vapor phase experiments performed with a synthetic crude reductive carbonylation product prepared by mixing DMA (obtained from a commercial supplier) with methanol and water. The liquid feed was prepared by combining 100.81 g of methanol with 70.88 g of DMA and 28.35 g of water. The weight percent composition of this feed, as determined by the GC procedures described above, is summarized in Table 7.

TABLE 7

Weight percent composition of synthetic methanol reductive carbonylation product.

| | Acetaldehyde | Water | Acetaldehyde Dimethyl Acetal | Methyl Acetate | Methanol | Ethanol | Crotonaldehyde |
|---|---|---|---|---|---|---|---|
| Wt. % | 0.00 | 13.45% | 35.6% | 0.00 | 53.45% | 0.00 | 0.00 |
| mmoles | 0.0 | 1493.1 | 790.2 | 0.0 | 3337.1 | 0.0 | 0.0 |

MeOH equiv. = 4917.6 mmol
EtOH equiv. = 790.2 mmol
MeOH equiv./EtOH equiv. = 6.2 mmol Example 8

The catalyst charge used in this example consisted of 2.19 g (2.5 mL) of the 27% V$_2$O$_5$/TiO$_2$ catalyst described in Example 1. The vapor phase condensation reaction with the synthetic methanol reductive carbonylation feed was performed in a 25 mm outer diameter (21 mm inner diameter) quartz reactor tube with length=79 cm (31 inches). Heat to the reactor was provided by an Applied Test Systems series 3210 three element electric furnace having a heated zone 54 cm (21.25 inches) in length. Liquid products were collected in a three necked flask fitted with a glycol chilled (0° C.) jacket and an additional dry ice trap. The third neck of the flask was connected to a side arm which was connected to a dry ice trap. The base of the main receiver flask and dry ice trap were fitted with a stopcock to allow for draining of the liquid products.

The quartz reactor had indentations 16 cm (6.25 inches) up from the base of the tube. The region of the reactor with the indentations was situated near the base of the heated section of the furnace. The reactor was also fitted with a thermowell that extended from the top of the reactor to about an inch below the indentations. The reactor was first loaded with quartz chips to about 8 inches in height above the indentations to allow the catalyst to be positioned in the middle of the 3 element furnace. The reactor was then loaded with the catalyst charge. The three point thermocouple in the thermowell was placed 1.5 inches up from the base of the catalyst bed. Sufficient quartz chips were added to the region above the catalyst charge to reach the top of the heated region of the 3 element furnace.

The reactor temperature was set to 350° C. and the synthetic methanol reductive carbonylation feed was delivered at a rate of 0.4 mL/min with a nitrogen flow of 40 mL/min. Liquid samples were collected over a measured time period, then weighed and analyzed by gas chromatography using the procedures described above. The weight percent product composition is summarized in Table 8. The space-time-yield of the combined millimoles of isobutyraldehyde and isobutanol is summarized in Table 9. This example demonstrates that the majority of the DMA is converted in this reaction with only 1.01 wt % remaining in the product. The desired isobutyraldehyde product formed in 0.82 wt % concentration and at a rate of 780 STY.

Example 9

Example 8 was repeated except that the reactor temperature was set to 325° C. and 5 g (8 mL) of a 2.5% vanadium on titania catalyst was used (2.5% V/TiO$_2$). The catalyst was prepared by dissolving 0.6 g of ammonium metavandate in 120 mL of water at 40° C. After one hour of stirring at 40° C., the solution turned light yellow in color indicating complete dissolution of NH$_4$VO$_3$ in water. About 10 g of the crushed titania support (Saint Gobain-Norpro, Dms2011-0416) was added to the solution and stirred at 80° C. until the water was evaporated. Then, the resulting powder was dried overnight at 90° C. in an oven. The final color of the powder was observed to be yellow from initial white indicating the impregnation of vanadium on the support. The powder was pressed and sieved to 8×14 mesh for loading in the vapor phase reactor.

This example shows that the 2.5% V/TiO$_2$ catalyst is effective for converting DMA to isobutyraldehyde and isobutanol, which formed in 4.21 wt % and 1.2 wt % concentration and at a combined rate of 800 STY.

Example 10

Example 8 was repeated except that 5 g (7 mL) of a 3.3% vanadium oxide on titania catalyst was used (3.3% V$_2$O$_5$/TiO$_2$). The catalyst was prepared by spraying 20 g of the anatase rods (Aerolyst 7708 obtained from Evonik Industries) four times with about 9.1 g each time of a 3.8 wt. % aqueous solution of vanadyl oxalate (prepared from a 2:1 molar mixture of oxalic acid and ammonium metavanadate). The rods were dried at 200° C. in air for two hours between each impregnation then calcined at 500° C. for two hours in a muffle furnace in air after the final impregnation.

Results are shown in Table 8. This example shows that the 3.3% V$_2$O$_5$/TiO2 catalyst is effective for converting DMA to isobutyraldehyde an isobutanol, which formed in 3.48 wt % and 0.66 wt % concentration and at a rate of 1,360 STY.

TABLE 8

| Ex. | Water (wt %) | HAc (wt %) | MeOH (w t%) | EtOH (wt %) | Acrolein (wt %) | HPr (wt %) | iHBu (wt %) | Methacrolein (wt %) | DMA (wt %) | n-HBu (wt %) | MeOAc (wt %) | iBuOH (wt %) | HCr (wt %) | nBuOH (wt %) |
|---|---|---|---|---|---|---|---|---|---|---|---|---|---|---|
| 8 | 17.85 | 3.15 | 74.99 | 0.75 | 0.58 | 0.25 | 0.82 | 0.33 | 1.01 | 0.09 | 0.00 | 0.00 | 0.18 | 0.00 |
| 9 | 71.85 | 0.70 | 19.62 | 0.39 | 0.00 | 0.38 | 4.21 | 0.20 | 0.34 | 0.15 | 0.00 | 1.20 | 0.77 | 0.18 |
| 10 | 35.72 | 4.08 | 51.39 | 0.73 | 0.42 | 0.49 | 3.48 | 1.00 | 1.46 | 0.00 | 0.24 | 0.66 | 0.32 | 0.00 |

TABLE 9

Space-time-yield (STY) of isobutyraldehyde and isobutanol formed from conversion of synthetic methanol reductive carbonylation product over heterogeneous mixed oxide catalysts.

| Example | Reactor Conditions | Catalyst Description | STY (mmole iHBu + iHBuOH/ Liter cat/h) |
|---|---|---|---|
| 8 | 350° C., 80 mL/min N2, 0.4 mL/min LFR | 27% $V_2O_5/TiO_2$ | 780 |
| 9 | 325° C., 80 mL/min N2, 0.4 mL/min LFR | 2.5% $V/TiO_2$ | 800 |
| 10 | 350° C., 80 mL/min N2, 0.4 mL/min LFR | 3.3% $V_2O_5/TiO_2$ | 1,360 |

Comparative Examples C1 to C3 and Examples 11-23

To demonstrate a number of embodiments that produce crude reductive carbonylation product that can be used in the Guerbet reaction, reductive carbonylation products were produced by a variety of processes. Except as indicated in connection with specific processes, the following procedures were used for each example. The stated quantity of catalyst $Co(OAc)_2$ $4H_2O$ (in Examples C1, C2), $CoI_2$ (cobalt (II) iodide in Example C3), or $Y_2CoI_4$ (where Y=$MePPh_3$ in Examples 11-14 and 16-23 and Y=PyMe in Example 15) was dissolved in methanol and charged to a Hastelloy autoclave along with the stated amounts of the phosphine ligand and/or promoter, where applicable. The ligand triphenylphosphine ($PPh_3$) was used in Examples C1-C3 and the ligand dppp was used in Examples 19-23). The promoter was methyl iodide (MeI) was used in examples C1, C2 and C3 and the promoter methyltriphenylphosphonium iodide ($MePPh_3I$) was used in Example 23. The stated amount of the solvent toluene was then added where applicable (i.e. Examples 16-18, 21-22). The autoclave was sealed and purged three times with nitrogen then pressurized to 69 bar (1000 psig) with 1:1 $CO:H_2$ and heated to the stated temperature. Upon reaching the stated temperature set point, the reactor was pressurized to a total pressure of 138 bar (2400 psig) or 276 bar (4000 psig) with 1:1 $CO:H_2$. Once the stated reaction time was reached the reactor was cooled to room temperature, vented and the product decanted. Composition was then measured by gas chromatography using the procedures described above. Results are presented in Table 10. Reaction conditions are presented in Table 11.

TABLE 10

$C_1$ and $C_2$ equivalents and MeI in product of reductive carbonylation of methanol.

| Ex | Catalyst | Catalyst Conc. | Promoter | Promoter Conc. | Ligand | Ligand Conc. | Methanol Conversion | Yield of Carbonylated Products | $C_1$ Equivalents (mmol) (i.e. $C_n$) | $C_2$ Equivalents (mmol) (i.e. $C_{n+1}$) | $C_1/C_2$ Mole Ratio | Mole % $C_2$ as DMA | STY ($Mh^{-1}$) | Wt % MeI in product |
|---|---|---|---|---|---|---|---|---|---|---|---|---|---|---|
| C1 | $Co(OAc)_2 4H_2O$ | 0.025% | MeI | 0.15% | PPh3 | 0.050% | 56% | 15.8% | 1167 | 205 | 5.7 | 74% | 2.7 | 0.11% |
| C2 | $Co(OAc)_2 4H_2O$ | 0.025% | MeI | 0.15% | PPh3 | 0.050% | 45% | 22.0% | 1023 | 299 | 3.4 | 57% | 6.5 | 0.09% |
| C3 | $CoI_2$ | 0.200% | MeI | 0.40% | PPh3 | 0.20% | 45% | 12.3% | 450 | 65 | 3.4 | 78% | 5.1 | 0.59% |
| 11 | $(MePPh_3)2CoI_4$ | 0.025% | n/a | n/a | n/a | 0.00% | 11.6% | 36.9% | 1012 | 136 | 7.5 | 83% | 5.3 | 0.00% |
| 12 | $(MePPh_3)_2CoI_4$ | 0.200% | n/a | n/a | n/a | 0.00% | 17.0% | 50% | 460 | 85 | 5.4 | 77% | 6.7 | 0.00% |
| 13 | $(MePPh_3)_2CoI_4$ | 0.200% | n/a | n/a | n/a | 0.00% | 33.9% | 73.0% | 650 | 332 | 2.0 | 39% | 13.1 | 0.00% |
| 14 | $(MePPh_3)_2CoI_4$ | 0.400% | n/a | n/a | n/a | 0.00% | 43.5% | 78.7% | 244 | 169 | 1.4 | 21% | 13.1 | 0.00% |
| 15 | $(PyMe)_2CoI_4$ | 0.200% | n/a | n/a | n/a | 0.00% | 16.8% | 53% | 870 | 171 | 5.1 | 77% | 6.7 | 0.00% |
| 16 | $(MePPh_3)_2CoI_4$ | 0.025% | n/a | n/a | n/a | 0.00% | 6.1% | 20.6% | 560 | 37 | 15.3 | 94% | 1.5 | 0.00% |
| 17 | $(MePPh_3)_2CoI_4$ | 0.200% | n/a | n/a | n/a | 0.00% | 15.3% | 47.9% | 485 | 91 | 5.3 | 87% | 3.6 | 0.00% |
| 18 | $(MePPh_3)_2CoI_4$ | 0.200% | n/a | n/a | n/a | 0.00% | 29.3% | 79.8% | 423 | 206 | 2.0 | 64% | 6.8 | 0.00% |
| 19 | $(MePPh_3)_2CoI_4$ | 0.200% | n/a | n/a | Dppp | 0.100% | 31.6% | 70.0% | 358 | 142 | 2.5 | 48% | 11.1 | 0.00% |
| 20 | $(MePPh_3)_2CoI_4$ | 0.200% | n/a | n/a | Dppp | 0.100% | 48.4% | 78.8% | 236 | 203 | 1.2 | 15% | 15.5 | 0.00% |
| 21 | $(MePPh_3)_2CoI_4$ | 0.200% | n/a | n/a | Dppp | 0.100% | 14.5% | 49.8% | 455 | 82 | 5.6 | 85% | 6.3 | 0.00% |
| 22 | $(MePPh_3)_2CoI_4$ | 0.200% | n/a | n/a | Dppp | 0.100% | 24.4% | 72.4% | 394 | 143 | 2.8 | 76% | 5.6 | 0.00% |
| 23 | $(MePPh_3)_2CoI_4$ | 0.0250% | $MePPh_3I$ | 0.35% | Dppp | 0.025% | 28.2% | 62.4% | 829 | 279 | 3.0 | 55% | 10.9 | 0.00% |

TABLE 11

Reaction conditions for the methanol reductive carbonylation experiments described in Table 10.

| Ex | Methanol (mmol) | 50 vol % Solvent | Reaction Time (h) | Temperature (° C.) | Pressure (psig) |
|---|---|---|---|---|---|
| C1 | 1483 | n/a | 1.25 | 175 | 2400 |
| C2 | 1483 | n/a | 0.75 | 190 | 4000 |
| C3 | 618 | n/a | 0.5 | 175 | 2400 |
| 11 | 1236 | n/a | 0.5 | 175 | 4000 |
| 12 | 618 | n/a | 0.5 | 175 | 2400 |
| 13 | 1236 | n/a | 0.5 | 175 | 4000 |
| 14 | 618 | n/a | 0.5 | 190 | 4000 |
| 15 | 1236 | n/a | 0.5 | 175 | 2400 |
| 16 | 618 | Toluene | 0.5 | 175 | 2400 |
| 17 | 618 | Toluene | 0.5 | 175 | 2400 |
| 18 | 742 | Toluene | 0.5 | 175 | 4000 |
| 19 | 618 | n/a | 0.5 | 175 | 2400 |
| 20 | 618 | n/a | 0.5 | 175 | 4000 |
| 21 | 618 | Toluene | 0.5 | 175 | 2400 |
| 22 | 618 | Toluene | 0.5 | 175 | 4000 |
| 23 | 1236 | n/a | 0.5 | 175 | 4000 |

The invention has been described in detail with particular reference to certain embodiments thereof, but it will be understood that variations and modifications can be effected within the spirit and scope of the invention. The forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention. The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A process comprising:
   (a) contacting hydrogen, carbon monoxide, and a primary alkyl alcohol having n carbon atoms in the presence of a carbonylation catalyst to form a crude reductive carbonylation product comprising at least one $C_{n+1}$ alcohol equivalent having (n+1) carbon atoms and at least one $C_n$ alcohol equivalent having n carbon atoms, wherein the reductive carbonylation catalyst comprises a complex of cobalt, iodide, and an onium cation or an alkali metal cation of the general formula $Y_2CoI_4$, wherein Y is the onium cation or the alkali metal cation;
   (b) contacting at least one $C_{n+1}$ alcohol equivalent and at least one $C_n$ alcohol equivalent with a Guerbet catalyst to form a product composition comprising at least one product molecule, wherein:
   n is selected from 1, 2 or 3;
   the total number of moles of the at least one $C_n$ alcohol equivalent contacted with the Guerbet catalyst is at least equal to the number of moles one $C_{n+1}$ alcohol equivalent contacted with the Guerbet catalyst and, if n=1, is equal to at least 2.0 multiplied by the number of moles one $C_{n+1}$ alcohol equivalent contacted with the Guerbet catalyst;
   contacting the at least one $C_n$ alcohol equivalent and the at least one $C_{n+1}$ alcohol equivalent with the Guerbet catalyst comprises contacting the crude reductive carbonylation product or a portion thereof with the Guerbet catalyst; and the at least one product molecule has the structure of formula IV:

wherein:
   C is a carbon atom;
   H is a hydrogen atom;
   Q is an alcohol or aldehyde group having one carbon;
   R is a linear alkyl group having n carbon atoms; and
   T is an alkyl group having (n−1) carbon atoms, except that when n=1, T is methyl.

2. The process of claim 1, wherein n is 1.

3. The process of claim 1, wherein the product composition comprises at least about 5.0 moles of product compound in which Q is an aldehyde group having one carbon for every mole of product compound in which Q is an alcohol group having one carbon.

4. The process of claim 1, wherein the total number of moles of $C_n$ alcohol equivalents in the crude reductive carbonylation product is at least equal to the total number of moles of $C_{n+1}$ alcohol equivalents in the crude reductive carbonylation product and, if n=1, is equal to at least 2.0 multiplied by the total number of moles of $C_{n+1}$ alcohol equivalent in the crude reductive carbonylation product.

5. The process of claim 1, wherein contacting the at least one $C_{n+1}$ alcohol equivalent and at least one $C_n$ alcohol equivalent with the Guerbet catalyst comprises contacting at least some supplemental $C_n$ alcohol equivalent with the Guerbet catalyst.

6. The process of claim 1, wherein the crude reductive carbonylation product or portion thereof that is contacted with the Guerbet catalyst comprises a dialkyl acetal of an aldehyde, the aldehyde being a linear alkyl aldehyde having (n+1) carbon atoms, and the dialkyl acetal comprising two linear alkoxy groups having n carbon atoms.

7. The process of claim 6, wherein n=1.

8. The process of claim 6, wherein the dialkyl acetal of the linear alkyl aldehyde comprises at least about 30 molar percent of the total number of $C_{n+1}$ alcohol equivalents present in the crude reductive carbonylation product or portion thereof that is contacted with the Guerbet catalyst.

9. The process of claim 6, wherein alkoxy groups on the dialkyl acetal of the linear alkyl aldehyde comprise at least about 5 molar percent of the total number of $C_n$ alcohol equivalents present in the crude reductive carbonylation product or portion thereof that is contacted with the Guerbet catalyst.

10. The process of claim 1, further comprising separating at least some of the crude reductive carbonylation product from the reductive carbonylation catalyst by vaporization prior to contacting the at least one $C_n$ alcohol equivalent and the at least one $C_{n+1}$ alcohol equivalent with the Guerbet catalyst.

11. The process of claim 1, wherein the Guerbet catalyst is in a solid phase when it is contacted with the at least one $C_n$ alcohol equivalent and the at least one $C_n$ alcohol equivalent.

12. The process of claim 11, wherein the Guerbet catalyst comprises a material selected from heterogeneous vanadium oxide supported on titania, palladium oxide supported on titania, or copper oxide-zinc oxide supported on alumina.

13. The process of claim 1, wherein the Guerbet catalyst is in a liquid phase when it is contacted with the at least one $C_n$ alcohol equivalent and the at least one $C_n$ alcohol equivalent.

14. The process of claim 13, wherein the Guerbet catalyst comprises:
a material selected from [IrCl(cod)]$_2$, [Cp*IrCl$_2$]$_2$, [Ir(OH)(cod)]$_2$, IrCl(PPh$_3$)$_3$, IrCl$_3$($_3$H$_2$O), RhCl$_3$/PBu$_3$, PdCl$_2$, [RuCl(eta6-p-cymene)]Cl, PdCl$_2$ and RuCl$_2$;
a co-catalyst selected from alkali metal alkoxide co-catalysts; and
optionally, an organophosphorus ligand.

15. The process of claim 1, wherein the onium cation is of the general formula (I) or (II):

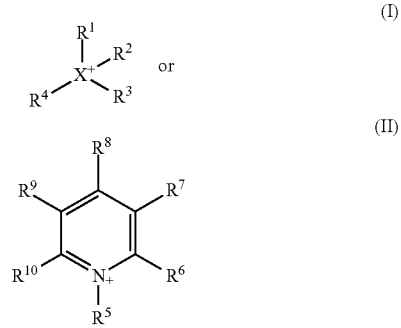

wherein X is selected from the group consisting of phosphorus (P) and nitrogen (N), $R^1$ is methyl, and $R^2$, $R^3$, and $R^4$ are independently selected from alkyl having up to 12 carbon atoms and aryl, wherein said aryl is selected from only one of the group consisting of phenyl, tolyl, xylyl, and mesityl; $R^5$ is methyl and $R^6$, $R^7$, $R^8$, $R^9$, and $R^{10}$ are hydrogen.

16. The process of claim 1, wherein the reductive carbonylation catalyst further comprises a phosphine ligand of the general formula

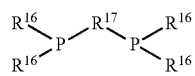

wherein phosphorus atoms P are bridged by 2 to 6 atoms of $R^{17}$, wherein $R^{17}$ is selected from the group consisting of substituted or unsubstituted alkylene, cycloalkylene, arylene, and biarylene, each having up to 20 carbon atoms; wherein a heteroatom, optionally, can substitute for one or more of said carbon atoms, wherein said heteroatom is selected from the group consisting of nitrogen, oxygen, sulfur, and phosphorus; and
$R^{16}$ is selected from the group consisting of substituted or unsubstituted alkyl, alkoxy, cycloalkyl, aryl, and aryloxy, each having up to 20 carbon atoms.

17. The process of claim 15, wherein the phosphine ligand is of the general formula

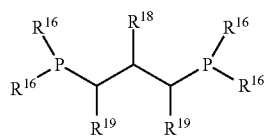

wherein $R^{18}$ is selected from the group consisting of a hydrogen radical and a hydrocarbon radical having up to 17 carbon atoms, wherein said hydrocarbon radical can be substituted with at least one substituent selected from the group consisting of alkyl, alkoxy, cycloalkyl, aryl, aryloxy, dialkylphosphinomethyl, and diarylphosphinomethyl; and
$R^{19}$ is selected from the group consisting of hydrogen radical, and substituted or unsubstituted alkyl, alkoxy, cycloalkyl, aryl, and aryloxy, each having up to 8 carbon atoms.

18. The process of claim 1, wherein the reductive carbonylation catalyst further comprises a phosphonium iodide.

19. The process of claim 1, wherein the crude reductive carbonylation product comprises less than 1 weight percent of methyl iodide, based on the total weight of said crude reductive carbonylation product.

20. A process comprising contacting at least one $C_n$ alcohol equivalent having n carbon atoms and at least one $C_{n+1}$ alcohol equivalent having (n+1) carbon atoms with a Guerbet catalyst to form a product composition comprising at least one product molecule, wherein:
the total number of moles of the at least one $C_n$ alcohol equivalent contacted with the Guerbet catalyst is at least equal to the number of moles one $C_{n+1}$ alcohol equivalent contacted with the Guerbet catalyst and, if n=1, is equal to at least 2.0 multiplied by the number of moles one $C_{n+1}$ alcohol equivalent contacted with the Guerbet catalyst;

n=1,2 or 3;

at least some of the at least one $C_n$ alcohol equivalent and at least some of the least one $C_{n+1}$ alcohol equivalent are within or derived from a crude reductive carbonylation product, the crude reductive carbonylation product being a product of contacting hydrogen, carbon monoxide, and a primary alkyl alcohol having n carbon atoms in the presence of a reductive carbonylation catalyst, the reductive carbonylation catalyst comprising a complex of cobalt, iodide, and an onium cation or an alkali metal cation of the general formula $Y_2CoI_4$, wherein Y is the onium cation or the alkali metal cation; and
the at least one product molecule has the structure of formula IV:

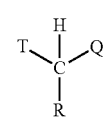

wherein:
C is a carbon atom;
H is a hydrogen atom;
Q is an alcohol or aldehyde group having one carbon;
R is a linear alkyl group having n carbon atoms; and
T is an alkyl group having (n–1) carbon atoms, except that when n=1, T is methyl.

21. The process of claim 20, wherein n is 1.

22. The process of claim 20, wherein the product composition comprises at least about 5.0 moles of product compound in which Q is an aldehyde group having one carbon for every mole of product compound in which Q is an alcohol group having one carbon.

23. The process of claim 20, wherein the total number of moles of $C_n$ alcohol equivalents in the crude reductive carbonylation product is at least equal to the total number of moles of $C_{n+1}$ alcohol equivalents in the crude reductive carbonylation product and, if n=1, is equal to at least 2.0 multiplied by the total number of moles of $C_{n+1}$ alcohol equivalent in the crude reductive carbonylation product.

24. The process of claim 20, wherein contacting the at least one $C_{n+1}$ alcohol equivalent and at least one $C_n$ alcohol equivalent with the Guerbet catalyst comprises contacting at least some supplemental $C_n$ alcohol equivalent with the Guerbet catalyst.

25. The process of claim 20, wherein the crude reductive carbonylation product or portion thereof that is contacted with the Guerbet catalyst comprises a dialkyl acetal of an aldehyde, the aldehyde being a linear alkyl aldehyde having (n+1) carbon atoms, and the dialkyl acetal comprising two linear alkoxy groups having n carbon atoms.

26. The process of claim 25, wherein n=1.

27. The process of claim 25, wherein the dialkyl acetal of the linear alkyl aldehyde comprises at least about 30 molar percent of the total number of $C_{n+1}$ alcohol equivalents present in the crude reductive carbonylation product.

28. The process of claim 25, wherein alkoxy groups on the dialkyl acetal of the linear alkyl aldehyde comprise at least about 5 molar percent of the total number of $C_n$ alcohol equivalents present in the crude reductive carbonylation product.

29. The process of claim 20, further comprising separating at least some of the crude reductive carbonylation product from the reductive carbonylation catalyst by vaporization prior to contacting the at least one $C_n$ alcohol equivalent and the at least one $C_{n+1}$ alcohol equivalent with the Guerbet catalyst.

30. The process of claim 20, wherein the Guerbet catalyst is in a solid phase when it is contacted with the at least one $C_n$ alcohol equivalent and the at least one $C_n$ alcohol equivalent.

31. The process of claim 30, wherein the Guerbet catalyst comprises a material selected from heterogeneous vanadium oxide supported on titania, palladium oxide supported on titania, or copper oxide-zinc oxide supported on alumina.

32. The process of claim 20, wherein the Guerbet catalyst is in a liquid phase when it is contacted with the at least one $C_n$ alcohol equivalent and the at least one $C_n$ alcohol equivalent.

33. The process of claim 32, wherein the Guerbet catalyst comprises:
a material selected from [IrCl(cod)]$_2$, [Cp*IrCl$_2$]$_2$, [Ir(OH)(cod)]$_2$, IrCl(PPh$_3$)$_3$, IrCl$_3$($_3$H$_2$O), RhCl$_3$/PBu$_3$, PdCl$_2$, [RuCl(eta6-p-cymene)]Cl, PdCl$_2$ and RuCl$_2$;
a co-catalyst selected from alkali metal alkoxide co-catalysts; and
optionally, an organophosphorus ligand.

34. The process of claim 20, wherein the onium cation is of the general formula (I) or (II):

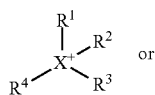
(I)

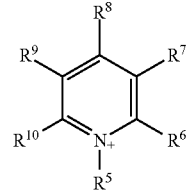
(II)

wherein X is selected from the group consisting of phosphorus (P) and nitrogen (N), $R^1$ is methyl, and $R^2$, $R^3$, and $R^4$ are independently selected from alkyl having up to 12 carbon atoms and aryl, wherein said aryl is selected from only one of the group consisting of phenyl, tolyl, xylyl, and mesityl; $R^5$ is methyl and $R^6$, $R^7$, $R^8$, $R^9$, and $R^{10}$ are hydrogen.

35. The process of claim 20, wherein the reductive carbonylation catalyst further comprises a phosphine ligand of the general formula

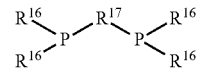

wherein phosphorus atoms P are bridged by 2 to 6 atoms of $R^{17}$, wherein $R^{17}$ is selected from the group consisting of substituted or unsubstituted alkylene, cycloalkylene, arylene, and biarylene, each having up to 20 carbon atoms; wherein a heteroatom, optionally, can substitute for one or more of said carbon atoms, wherein said heteroatom is selected from the group consisting of nitrogen, oxygen, sulfur, and phosphorus; and
$R^{16}$ is selected from the group consisting of substituted or unsubstituted alkyl, alkoxy, cycloalkyl, aryl, and aryloxy, each having up to 20 carbon atoms.

36. The process of claim 34, wherein the phosphine ligand is of the general formula

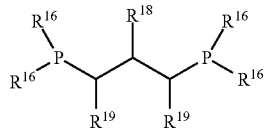

wherein $R^{18}$ is selected from the group consisting of a hydrogen radical and a hydrocarbon radical having up to 17 carbon atoms, wherein said hydrocarbon radical can be substituted with at least one substituent selected from the group consisting of alkyl, alkoxy, cycloalkyl, aryl, aryloxy, dialkylphosphinomethyl, and diarylphosphinomethyl; and
$R^{19}$ is selected from the group consisting of hydrogen radical, and substituted or unsubstituted alkyl, alkoxy, cycloalkyl, aryl, and aryloxy, each having up to 8 carbon atoms.

37. The process of claim 20, wherein the reductive carbonylation catalyst further comprises a phosphonium iodide.

38. The process of claim 1, wherein the crude reductive carbonylation product comprises less than 1 weight percent of methyl iodide, based on the total weight of said crude reductive carbonylation product.

39. A process comprising contacting at least one dialkyl acetal compound with a Guerbet catalyst to form a product composition comprising at least one product molecule, wherein the dialkyl acetal compound is the dialkyl of a linear alkyl aldehyde having (n+1) carbon atoms, and the dialkyl acetal comprises two linear alkoxy groups having n carbon atoms, and n=1, 2 or 3; and the at least one product molecule has the structure of formula IV:

IV wherein:
C is a carbon atom;
H is a hydrogen atom;
Q is an alcohol or aldehyde group having one carbon;
R is a linear alkyl group having n carbon atoms; and
T is an alkyl group having (n−1) carbon atoms, except that when n=1, T is methyl.

40. The process of claim 39, wherein the contacting of the at least one dialkyl acetal compound with the Guerbet catalyst occurs in the presence of water.

41. The process of claim 39, wherein n is 1.

42. The process of claim 39, wherein contacting the dialkyl acetal with the Guerbet catalyst comprises contacting at least some supplemental $C_n$ alcohol equivalent having n carbon atoms with the Guerbet catalyst.

43. The process of claim 39, wherein the product composition comprises at least about 5.0 moles of product compound in which Q is an aldehyde group having one carbon for every mole of product compound in which Q is an alcohol group having one carbon.

44. The process of claim 39, wherein the Guerbet catalyst is in a solid phase when it is contacted with the at least one $C_n$ alcohol equivalent and the at least one $C_n$ alcohol equivalent.

45. The process of claim 44, wherein the Guerbet catalyst comprises a material selected from heterogeneous vanadium oxide supported on titania, palladium oxide supported on titania, or copper oxide-zinc oxide supported on alumina.

46. The process of claim 39, wherein the Guerbet catalyst is in a liquid phase when it is contacted with the at least one $C_n$ alcohol equivalent and the at least one $C_n$ alcohol equivalent.

47. The process of claim 46, wherein the Guerbet catalyst comprises:
a material selected from [IrCl(cod)]$_2$, [Cp*IrCl$_2$]$_2$, [Ir(OH)(cod)]$_2$, IrCl(PPh$_3$)$_3$, IrCl$_3$($_3$H$_2$O), RhCl$_3$/PBu$_3$, PdCl$_2$, [RuCl(eta6-p-cymene)]Cl, PdCl$_2$ and RuCl$_2$;
a co-catalyst selected from alkali metal alkoxide co-catalysts; and
optionally, an organophosphorus ligand.

* * * * *